(12) United States Patent
Gatayama

(10) Patent No.: US 12,226,252 B2
(45) Date of Patent: Feb. 18, 2025

(54) EVALUATION APPARATUS, EVALUATION METHOD, AND EVALUATION SYSTEM

(71) Applicant: CANON MEDICAL SYSTEMS CORPORATION, Otawara (JP)

(72) Inventor: Kazuki Gatayama, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 640 days.

(21) Appl. No.: 17/443,651

(22) Filed: Jul. 27, 2021

(65) Prior Publication Data

US 2022/0022838 A1    Jan. 27, 2022

(30) Foreign Application Priority Data

Jul. 27, 2020   (JP) ................................. 2020-126174
Jul. 27, 2021   (JP) ................................. 2021-122263

(51) Int. Cl.
*A61B 6/00*        (2024.01)
*G06T 7/00*        (2017.01)

(52) U.S. Cl.
CPC ............ *A61B 6/545* (2013.01); *G06T 7/0014* (2013.01); *G06T 2207/10116* (2013.01); *G06T 2207/30004* (2013.01); *G06T 2207/30168* (2013.01)

(58) Field of Classification Search
CPC .................. A61B 6/545; G06T 7/0014; G06T 2207/10116; G06T 2207/30004; G06T 2207/30168; G16H 30/20; G16H 30/40; G16H 40/67; G16H 50/50; G16H 70/20
See application file for complete search history.

(56) References Cited

U.S. PATENT DOCUMENTS

| | | | | |
|---|---|---|---|---|
| 2004/0013223 | A1* | 1/2004 | Yamazaki | A61B 6/032 378/4 |
| 2013/0089176 | A1* | 4/2013 | Nabatame | A61B 6/032 378/4 |
| 2013/0274537 | A1* | 10/2013 | Park | G16H 20/40 600/1 |
| 2014/0270053 | A1* | 9/2014 | Larson | A61B 6/5258 378/4 |
| 2017/0178319 | A1* | 6/2017 | Sugiura | G06F 3/04847 |
| 2017/0202534 | A1* | 7/2017 | Crotty | A61B 6/465 |
| 2017/0249428 | A1* | 8/2017 | Mayo | G16H 70/20 |
| 2020/0320705 | A1* | 10/2020 | Wiemker | A61B 6/5258 |

FOREIGN PATENT DOCUMENTS

WO    WO 2015/198680 A1    12/2015

* cited by examiner

*Primary Examiner* — Wassim Mahrouka
(74) *Attorney, Agent, or Firm* — Oblon, McClelland, Maier & Neustadt, L.L.P.

(57) ABSTRACT

An evaluation apparatus according to an embodiment includes processing circuitry. On the basis of performance information related to performance of a medical diagnostic imaging device and numerical information related to at least one evaluation item, the processing circuitry makes an evaluation of a first imaging plan used by the medical diagnostic imaging device, the numerical information conforming to a guideline related to imaging plans. On the basis of a result of the evaluation, the processing circuitry generates, from the first imaging plan, a second imaging plan conforming to the guideline. The processing circuitry outputs the second imaging plan.

27 Claims, 19 Drawing Sheets

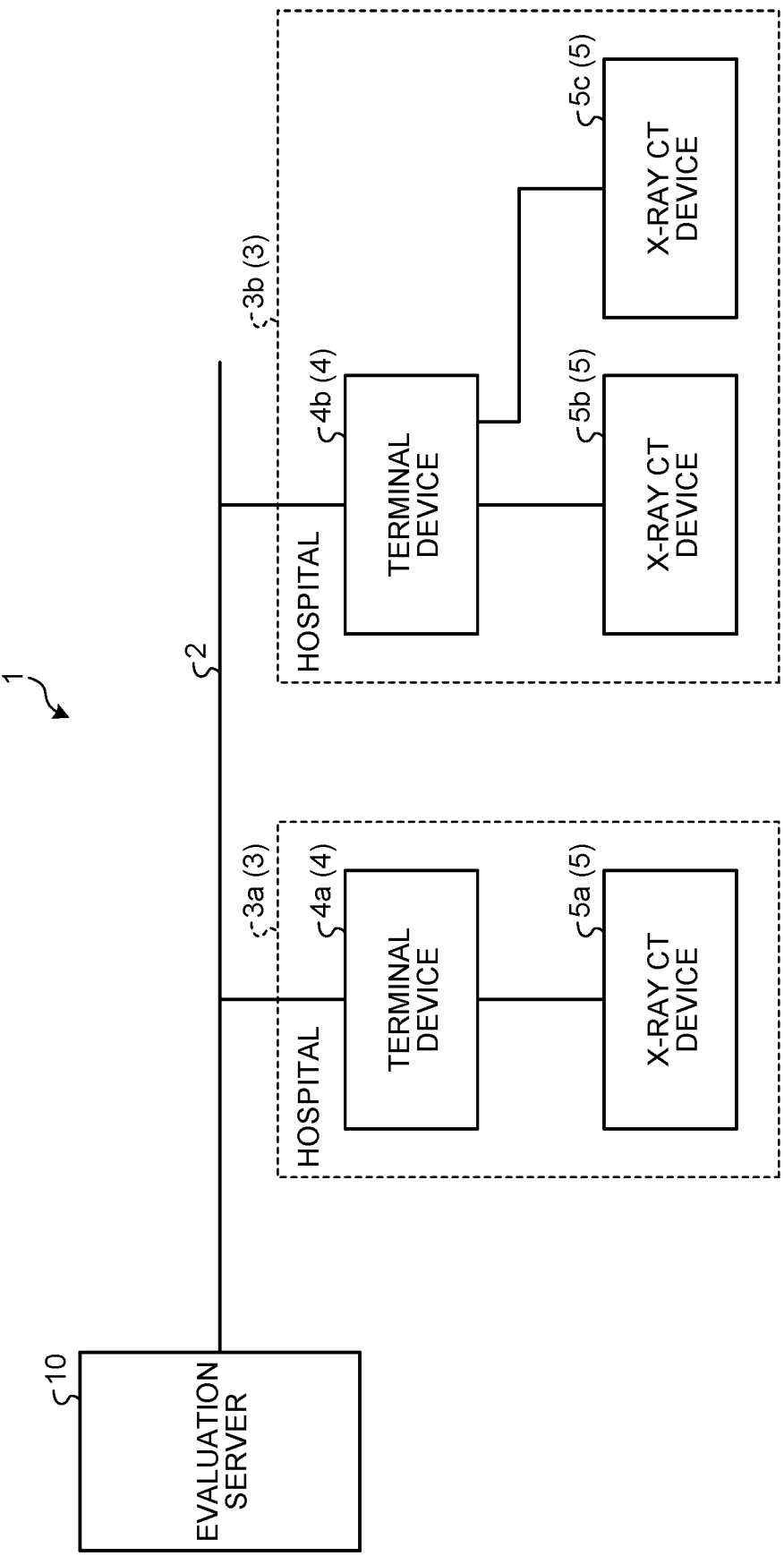

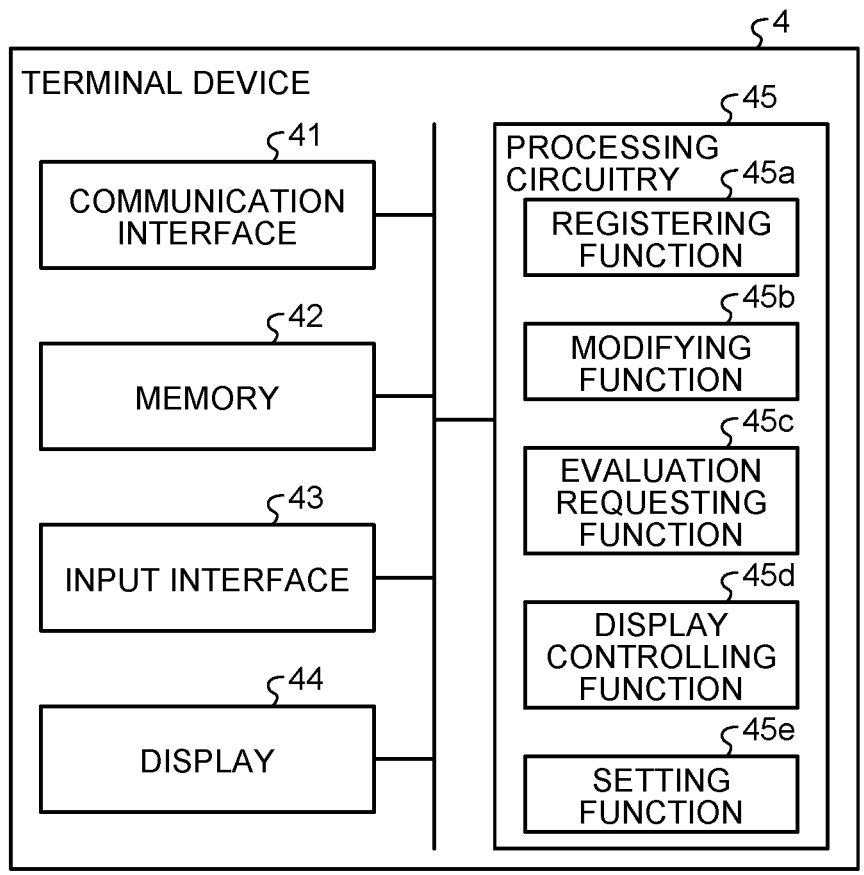

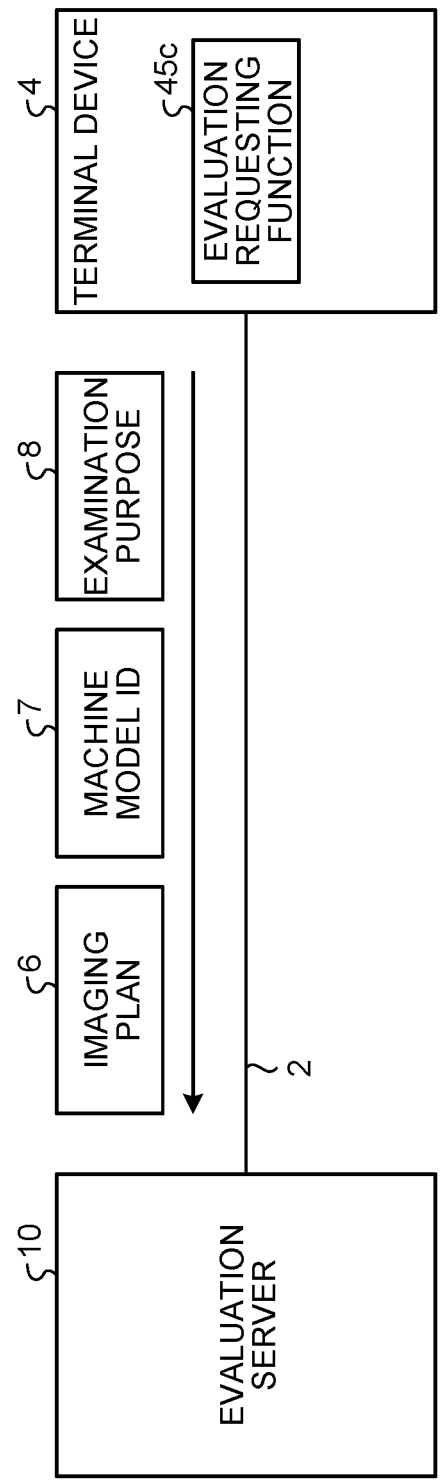

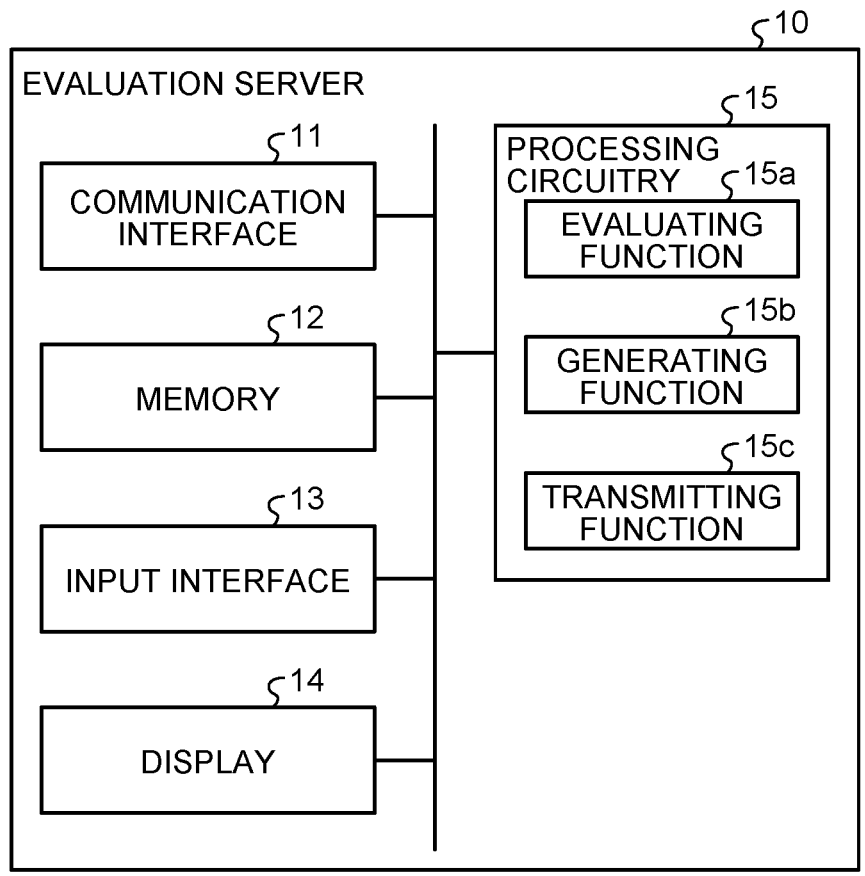

FIG.7

| MACHINE MODEL ID | PERFORMANCE INFORMATION |
|---|---|
| ... | ... |
| ⋮ | ⋮ |

12b

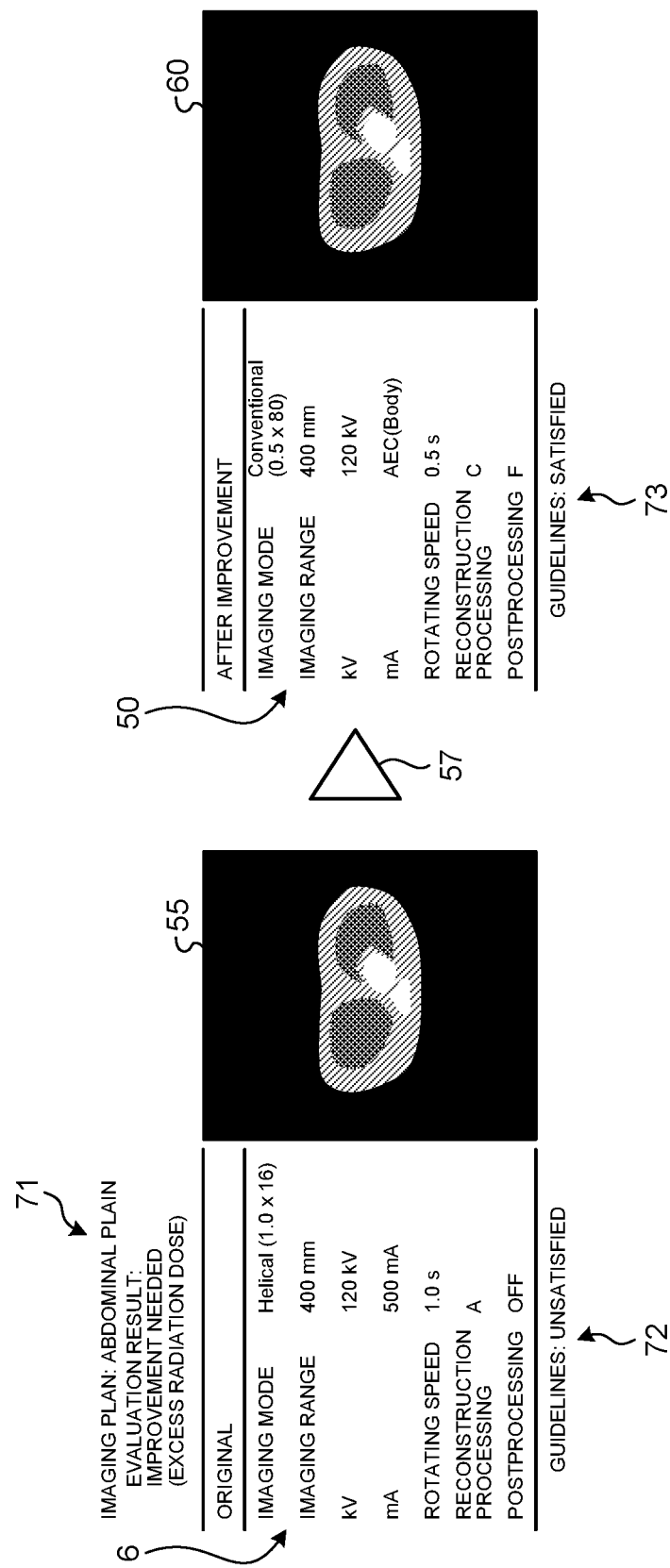

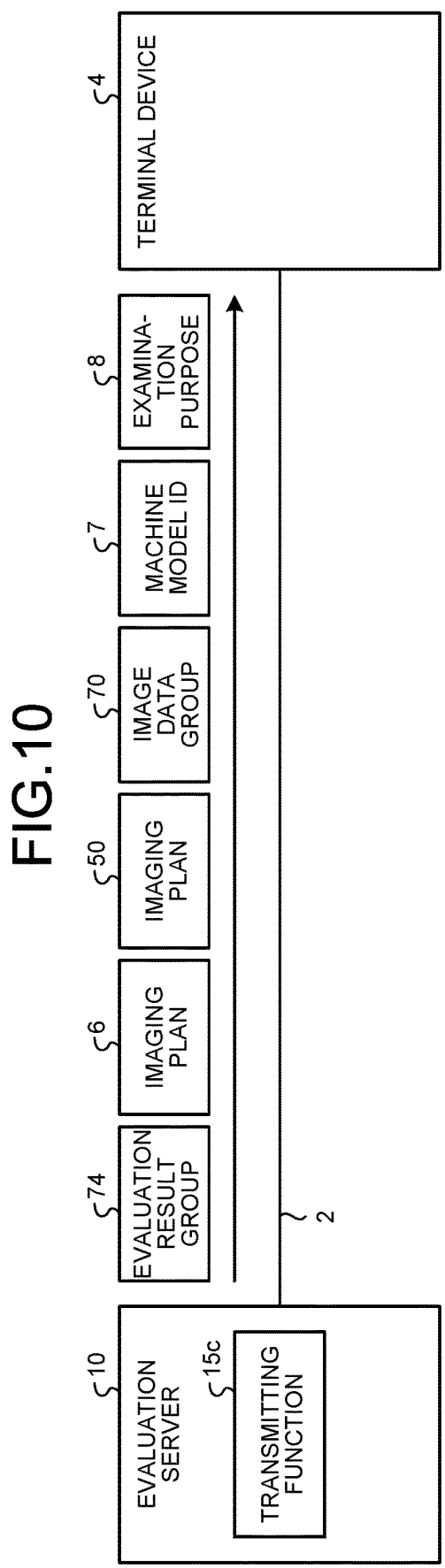

FIG.13A

| EXAMINATION PURPOSE | RANGE OF RADIATION DOSES | ANY UPDATE | DATE OF UPDATE |
|---|---|---|---|
| ... | ... | ... | ... |
| ⋮ | ⋮ | ⋮ | ⋮ |

| MACHINE MODEL ID | PERFORMANCE INFORMATION | ANY UPDATE | DATE OF UPDATE |
|---|---|---|---|
| ... | ... | ... | ... |
| ⋮ | ⋮ | ⋮ | ⋮ |

12b

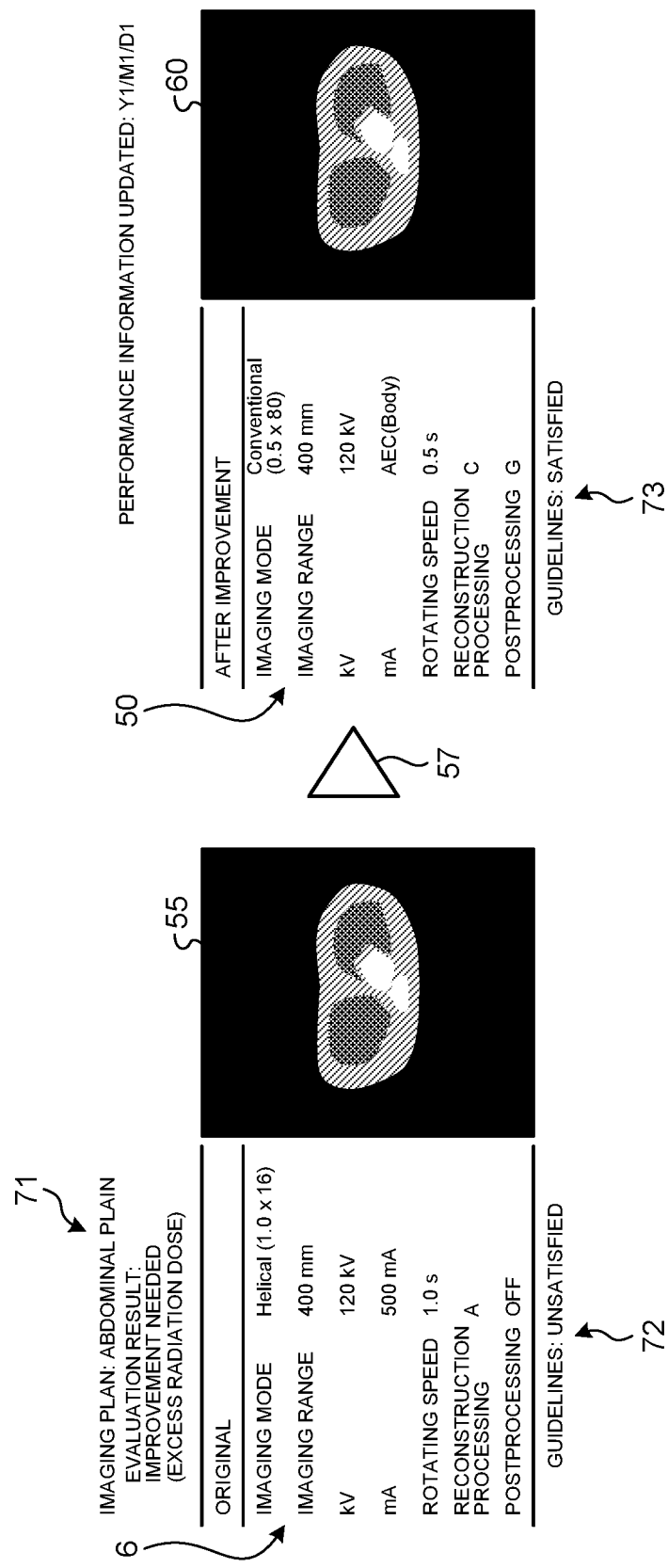

FIG.15A

| EXAMINATION PURPOSE | RANGE OF RADIATION DOSES | ANY UPDATE | DATE OF UPDATE | RANGE OF RADIATION DOSES BEFORE UPDATE |
|---|---|---|---|---|
| ⋮ | ⋮ | ⋮ | ⋮ | ⋮ |
| ⋯ | ⋯ | ⋯ | ⋯ | ⋯ |

| MACHINE MODEL ID | PERFORMANCE INFORMATION | ANY UPDATE | DATE OF UPDATE | PERFORMANCE INFORMATION BEFORE UPDATE | CONTENT OF UPDATE |
|---|---|---|---|---|---|
| ... | ... | ... | ... | ... | ... |
| ... | ... | ... | ... | ... | ... |

IMAGING PLAN: ABDOMINAL PLAIN
EVALUATION RESULT:
IMPROVEMENT NEEDED
(EXCESS RADIATION DOSE)

71 ↙

| ORIGINAL | |
|---|---|
| IMAGING MODE | Helical (1.0 x 16) |
| IMAGING RANGE | 400 mm |
| kV | 120 kV |
| mA | 500 mA |
| ROTATING SPEED | 1.0 s |
| RECONSTRUCTION PROCESSING | A |
| POSTPROCESSING | OFF |

GUIDELINES: UNSATISFIED ← 72

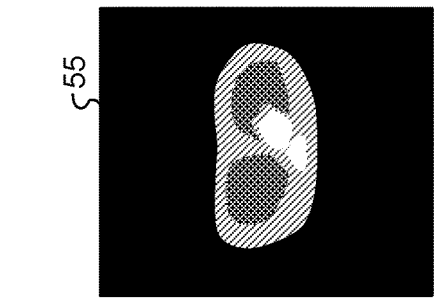
⟵ 55

6 ↗

△ ↙ 57

PERFORMANCE INFORMATION UPDATED: Y1/M1/D1
AFTER UPDATE

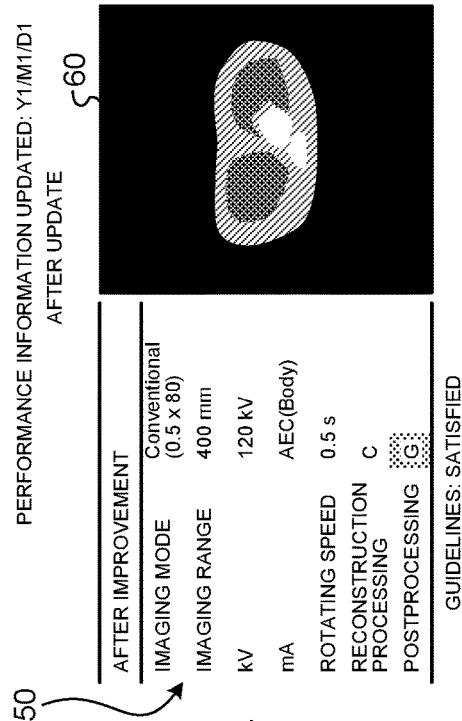 ⟵ 60

| AFTER IMPROVEMENT | |
|---|---|
| IMAGING MODE | Conventional (0.5 x 80) |
| IMAGING RANGE | 400 mm |
| kV | 120 kV |
| mA | AEC(Body) |
| ROTATING SPEED | 0.5 s |
| RECONSTRUCTION PROCESSING | C |
| POSTPROCESSING | G |

50 ↙

GUIDELINES: SATISFIED ← 73

BEFORE UPDATE

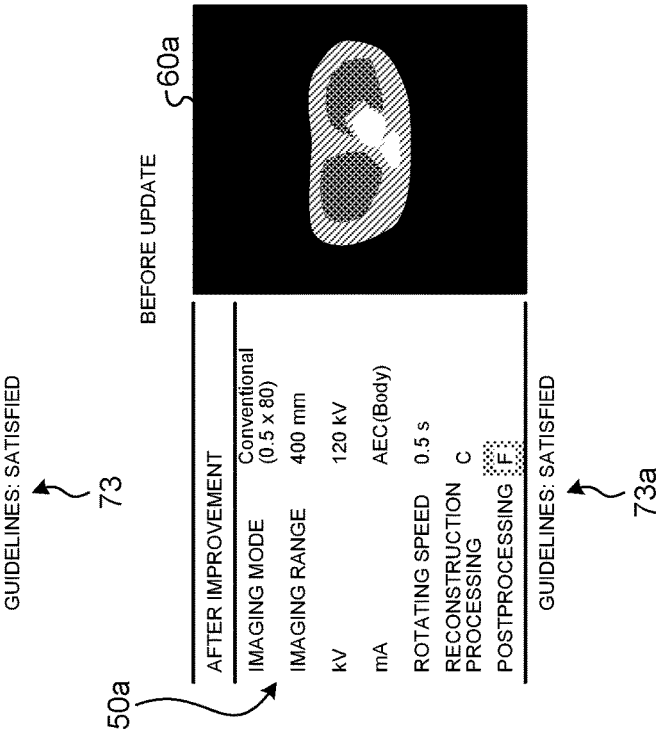 ⟵ 60a

| AFTER IMPROVEMENT | |
|---|---|
| IMAGING MODE | Conventional (0.5 x 80) |
| IMAGING RANGE | 400 mm |
| kV | 120 kV |
| mA | AEC(Body) |
| ROTATING SPEED | 0.5 s |
| RECONSTRUCTION PROCESSING | C |
| POSTPROCESSING | F |

50a ↙

GUIDELINES: SATISFIED ← 73a

| MACHINE MODEL ID | EXAMINATION PURPOSE | IMAGING PLAN | ANY MANUAL ADJUSTMENT | DATE OF MANUAL ADJUSTMENT |
|---|---|---|---|---|
| ... | ... | ... | ... | ... |
| ... | ... | ... | ... | ... |

| MACHINE MODEL ID | PERFORMANCE INFORMATION | NECESSITY OF EXECUTION OF EVALUATION |
|---|---|---|
| ... | ... | ... |
| ⋮ | ⋮ | ⋮ |

| TYPE OF HOSPITAL | REGION | PROGRAM |
|---|---|---|
| ... | ... | ... |
| ⋮ | ⋮ | ⋮ |

| TYPE OF DEVICE | PROGRAM |
|---|---|
| ... | ... |
| ⋮ | ⋮ |

81b

EVALUATION APPARATUS, EVALUATION METHOD, AND EVALUATION SYSTEM

CROSS-REFERENCE TO RELATED APPLICATIONS

This application is based upon and claims the benefit of priority from Japanese Patent Application No. 2020-126174, filed on Jul. 27, 2020 and Japanese Patent Application No. 2021-122263, filed on Jul. 27, 2021; the entire contents of which are incorporated herein by reference.

FIELD

Embodiments disclosed in this specification and the drawings are related to evaluation apparatuses, evaluation methods, and evaluation systems.

BACKGROUND

Imaging plans for X-ray computed tomography (CT) devices are generally managed by users, such as administrators of X-ray CT devices or clinical radiologists, for each of X-ray CT devices or each of institutions (for example, hospitals) where X-ray CT devices are installed. According to functions of the X-ray CT devices and circumstances at the facilities, the users determine and manage the imaging plans. Therefore, control of radiation doses of X-rays received by subjects and control of image quality of images generated by the X-ray CT devices are dependent on the skills and experience of the users.

BRIEF DESCRIPTION OF THE DRAWINGS

FIG. 1 is a diagram illustrating an example of a configuration of an evaluation system according to a first embodiment;

FIG. 2 is a diagram illustrating an example of a configuration of a terminal device according to the first embodiment;

FIG. 3 is a diagram illustrating an example of a data structure of an imaging plan database according to the first embodiment;

FIG. 4 is a diagram for explanation of an example of processing executed by an evaluation requesting function according to the first embodiment;

FIG. 5 is a diagram illustrating an example of a configuration of an evaluation server according to the first embodiment;

FIG. 6 is a diagram illustrating an example of a data structure of a guideline database according to the first embodiment;

FIG. 7 is a diagram illustrating an example of a data structure of a performance information database according to the first embodiment;

FIG. 9 is a diagram for explanation of an example of processing executed by the evaluation server according to the first embodiment;

FIG. 10 is a diagram for explanation of an example of processing executed by the evaluation server according to the first embodiment;

FIG. 13A is a diagram illustrating an example of a data structure of a guideline database according to a third modified example of the first embodiment;

FIG. 13B is a diagram illustrating an example of a data structure of a performance information database according to the third modified example of the first embodiment;

FIG. 14 is a diagram illustrating an example of display according to the third modified example of the first embodiment;

FIG. 15A is a diagram illustrating an example of a data structure of a guideline database according to a fourth modified example of the first embodiment;

FIG. 15B is a diagram illustrating an example of a data structure of a performance information database according to the fourth modified example of the first embodiment;

FIG. 16 is a diagram illustrating an example of display according to the fourth modified example of the first embodiment;

FIG. 17 is a diagram illustrating an example of a data structure of an imaging plan database according to a seventh modified example of the first embodiment;

FIG. 20A is a diagram illustrating an example of a data structure of a program database according to a tenth modified example of the first embodiment; and FIG. 20B is a diagram illustrating an example of a data structure of a program database according to an eleventh modified example of the first embodiment.

DETAILED DESCRIPTION

Figure 8A:
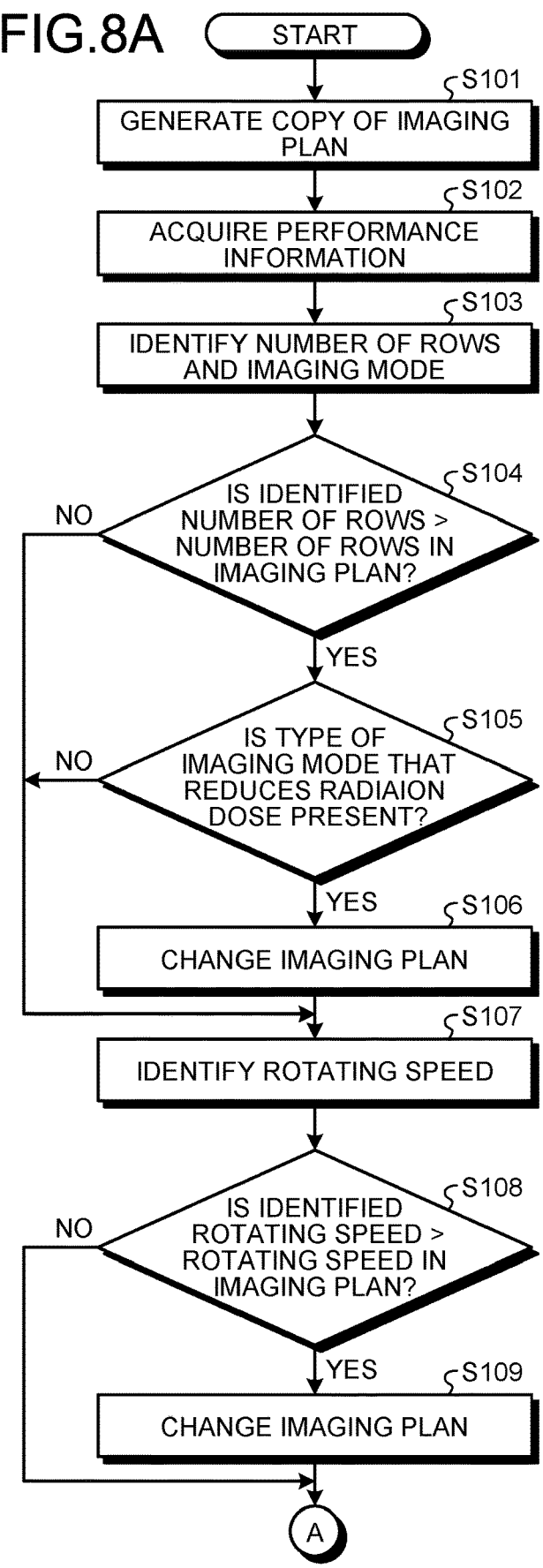
FIG. 8A is a flowchart illustrating an example of a flow of a process executed by the evaluation server according to the first embodiment.

An evaluation apparatus according to an embodiment includes processing circuitry. On the basis of performance information related to performance of a medical diagnostic imaging device and numerical information related to at least one evaluation item, the processing circuitry makes an evaluation of a first imaging plan used by the medical diagnostic imaging device, the numerical information conforming to guidelines related to imaging plans. On the basis of a result of the evaluation, the processing circuitry generates, from the first imaging plan, a second imaging plan conforming to the guidelines. The processing circuitry outputs the second imaging plan.

Embodiment of an evaluation apparatus, an evaluation method, and an evaluation system will be described in detail below while reference is made to the appended drawings. The evaluation apparatus, the evaluation method, and the evaluation system according to the present application are not limited by the embodiments described below. The embodiments may be combined with any other embodiment or conventional technique without any inconsistencies. In the following description, the same reference sign will be assigned to elements that are the same and any redundant explanation thereof may thus be omitted.

First Embodiment

FIG. 1 is a diagram illustrating an example of a configuration of an evaluation system 1 according to a first embodiment. As illustrated in FIG. 1, the evaluation system 1 includes an evaluation server 10, two terminal devices 4a and 4b, and three X-ray CT devices 5a to 5c. The evaluation server 10 is an example of an evaluation apparatus. The numbers of the devices included in the evaluation system 1 are not limited to the above numbers. The evaluation server 10 and the terminal devices 4a and 4b are communicably connected to each other via a network 2. The terminal device 4a and the X-ray CT device 5a are communicably connected to each other via a network. The terminal device 4b and the X-ray CT devices 5b and 5c are communicably connected to each other via a network.

The terminal device 4a and the X-ray CT device 5a are installed in a hospital 3a. The terminal device 4b and the X-ray CT devices 5b and 5c are installed in a hospital 3b different from the hospital 3a. The hospitals 3a and 3b will each be referred to as a "hospital 3" when the hospitals 3a and 3b are not differentiated from each other. Furthermore, the terminal devices 4a and 4b will each be referred to as a "terminal device 4" when the terminal devices 4a and 4b are not differentiated from each other. In addition, the X-ray CT devices 5a, 5b, and 5c will each be referred to as an "X-ray CT device 5" when the X-ray CT devices 5a, 5b, and 5c are not differentiated from each other. An X-ray CT device 5 is an example of a medical diagnostic imaging device.

The X-ray CT device 5 images a subject, generates CT image data representing a CT image, and generates, from the CT image data, image data (postprocessed image data) representing an image (a postprocessed image). For example, the X-ray CT device 5 includes a gantry, processing circuitry, an input interface, a memory, and a display. The gantry includes an X-ray tube, an X-ray detector, a rotating frame, and a data acquisition system (DAS).

For example, the X-ray tube generates X-rays to be emitted to a subject. The X-ray detector detects X-rays that have passed through the subject and outputs an electric signal corresponding to an X-ray dosage detected, to the DAS. The rotating frame is an annular frame that supports the X-ray tube and the X-ray detector oppositely to each other and rotates the X-ray tube and the X-ray detector.

The DAS generates detection data by amplifying the electric signal output from the X-ray detector and converting the amplified electric signal, which is an analog signal, into a digital signal. The DAS outputs the generated detection data to the processing circuitry. The processing circuitry performs preprocessing, such as logarithmic transformation processing, offset correction processing, interchannel sensitivity correction processing, and beam hardening correction processing, on the detection data. The preprocessed detection data are called raw data. The processing circuitry generates three-dimensional CT image data by performing reconstruction processing using, for example, a filtered back projection method or a successive approximation reconstruction method, on the raw data. The processing circuitry then generates image data by performing various types of image processing (postprocessing) on the CT image data. For example, on the basis of, for example, an input operation received from a user, such as an administrator or a clinical radiologist, via the input interface, the processing circuitry converts the CT image data into multiplanar reconstruction (MPR) image data, three-dimensional image data, or maximum intensity projection (MIP) image data, of any cross section, by a known method. That is, on the basis of the CT image data, the processing circuitry generates various image data, such as MPR image data, three-dimensional image data, or MIP image data. The processing circuitry then causes an image based on the image data to be displayed on a display. The processing circuitry is implemented by, for example, a processor.

The X-ray CT device 5 performs imaging on the basis of an imaging plan and generates, on the basis of the imaging plan, CT image data and image data. For example, the memory in the X-ray CT device 5 stores plural imaging plans respectively in association with plural examination purposes. For example, the memory is implemented by, for example, a semiconductor memory device such as a flash memory, a hard disk, or an optical disk. The memory is an example of a storage unit. The processing circuitry in the X-ray CT device 5 acquires an imaging plan from the memory, the imaging plan corresponding to an examination purpose received from a user via the input interface. The X-ray CT device 5 performs imaging on the basis of the imaging plan acquired.

The imaging plan includes imaging conditions, reconstruction conditions, and postprocessing conditions. An imaging plan is, for example, information required for the X-ray CT device 5 to operate in a sequential flow of an examination. The imaging plan is information used by the X-ray CT device 5. In a case where contrast radiography is performed, the imaging plan may include contrast imaging conditions and time information indicating imaging timings, in addition to those imaging conditions, reconstruction conditions, and postprocessing conditions. The imaging conditions include an imagine mode, a tube voltage, a tube current, an imaging range, and a rotating speed. The imaging mode indicates a scan mode, such as a helical scan mode, a conventional scan mode, or a step-and-shoot mode. The rotating speed is a time period required for the rotating frame to rotate by one turn. In a case where the X-ray CT device 5 performs auto-exposure control (AEC), the imaging conditions include execution of AEC.

The reconstruction conditions include a type of the reconstruction processing (a reconstruction algorithm) used in reconstruction of the CT image data. The postprocessing conditions include a type of the postprocessing used in generation of the image data.

The processing circuitry of the X-ray CT device 5 according to this embodiment stores an imaging plan into a memory and modifies or updates an imaging plan already stored in the memory, by being controlled by a terminal device 4, as described later.

The terminal device 4 is a device that manages imaging plans used when the X-ray CT device 5 performs imaging. For example, the terminal device 4a manages imaging plans for the X-ray CT device 5a, and the terminal device 4b manages imaging plans for the X-ray CT devices 5b and 5c. That is, the X-ray CT device 5a is a target to be managed (a management target) for the terminal device 4a, and the X-ray CT devices 5b and 5c are management targets for the terminal device 4b.

For example, the terminal device 4 is implemented by a computer, such as a server, a work station, a personal computer, or a tablet device. FIG. 2 is a diagram illustrating an example of a configuration of the terminal device 4 according to the first embodiment. The terminal device 4 includes a communication interface 41, a memory 42, an input interface 43, a display 44, and processing circuitry 45.

The communication interface 41 is connected to the processing circuitry 45 and controls communication between the terminal device 4 and the X-ray CT device 5 and communication between the terminal device 4 and the evaluation server 10. For example, the communication interface 41 receives various data and information from the X-ray CT device 5 and the evaluation server 10, and transmits the received data and information to the processing circuitry 45. Furthermore, for example, the communication interface 41 transmits various data and information to the X-ray CT device 5 and the evaluation server 10. The communication interface 41 is implemented by, for example, a network card, a network adapter, or a network interface controller (NIC).

The memory 42 is connected to the processing circuitry 45 and stores various data and information. FIG. 3 is a diagram illustrating an example of a data structure of an imaging plan database 42a according to the first embodiment. For example, the memory 42 stores the imaging plan database 42a illustrated in FIG. 3. The imaging plan database 42a has, registered therein, the most recent imaging plans for each of types of the X-ray CT devices 5 to be managed by the terminal device 4. Furthermore, the imaging plan database 42a has, registered therein, the most recent imaging plans for the X-ray CT devices 5, for each examination purpose. As illustrated in FIG. 3, the imaging plan database 42a has, registered therein plural records each having an item, "Machine Model Identification (ID)", an item, "Examination Purpose", and an item, "Imaging Plan".

For the item, "Machine Model ID", the identifier (machine model ID) indicating the types of the X-ray CT device 5 to be managed is registered. For the item, "Examination Purpose", the examination purpose is registered. For the item, "Imaging Plan", the imaging plan corresponding to the X-ray CT device 5 indicated by the machine model ID and the examination purpose is registered. The machine model ID, examination purpose, and imaging plan are registered in association with one another in the imaging plan database 42a by a registering function 45a described later. Furthermore, the imaging plans registered in the imaging plan database 42a are modified by a modifying function 45b described later.

The memory 42 stores programs for the processing circuitry 45 to implement various functions. For example, the memory 42 is implemented by, for example, a semiconductor memory device, such as a flash memory, a hard disk, or an optical disk. The memory 42 is an example of a storage unit.

The input interface 43 is connected to the processing circuitry 45 and receives input operations for various instructions, requests, and information from a user. For example, the input interface 43 converts an input operation received from a user into an electric signal and transmits the electric signal to the processing circuitry 45. For example, the input interface 43 is implemented by a trackball, a switch button, a mouse, a keyboard, a touchpad by which an input operation is executed through a touch on an operation surface, a touch screen having a display screen and a touchpad that are integrated with each other, a contactless input circuit using an optical sensor, and a voice input circuit. In this specification, the input interface 43 is not necessarily an input interface having physical operation parts, such as a mouse and a keyboard. Examples of the input interface 43 also include electric signal processing circuitry that receives an electric signal corresponding to an input operation from an external input device provided separately from the terminal device 4 and transmits this electric signal to the processing circuitry 45.

The display 44 is connected to the processing circuitry 45 and displays various types of information and images. For example, the display 44 converts information and data transmitted from the processing circuitry 45 into electric signals for display and outputs the electric signals. For example, the display 44 is implemented by a liquid crystal monitor, a cathode ray tube (CRT) monitor, or a touch panel.

The processing circuitry 45 controls operation of the terminal device 4 according to an input operation received from a user via the input interface 43. For example, the processing circuitry 45 is implemented by a processor.

The processing circuitry 45 executes the registering function 45a, the modifying function 45b, an evaluation requesting function 45c, a display controlling function 45d, and a setting function 45e. The registering function 45a is an example of a registering unit. The modifying function 45b is an example of a modifying unit. The evaluation requesting function 45c is an example of an evaluation requesting unit. The display controlling function 45d is an example of a display controlling unit. The setting function 45e is an example of a setting unit.

Processing functions that the processing circuitry 45 has are each stored in the form of a program that is able to be executed by a computer, into the memory 42. That is, the processing functions including the registering function 45a, the modifying function 45b, the evaluation requesting function 45c, the display controlling function 45d, and the setting function 45e that are components of the processing circuitry 45 illustrated in FIG. 2 are stored in the memory 42, in the form of programs that are able to be executed by a computer. The processing circuitry 45 implements the functions respectively corresponding to the programs by reading the programs from the memory 42 and executing the read programs. In other words, the processing circuitry 45 that has read the programs has the functions illustrated in the processing circuitry 45 of FIG. 2.

The registering function 45a registers imaging plans into the imaging plan database 42a. For example, the registering function 45a registers a machine model ID, an examination purpose, and an imaging plan that are received from a user via the input interface 43, in association with one another, into the imaging plan database 42a. The machine model ID, the examination purpose, and the imaging plan are thereby added into the imaging plan database 42a.

The registering function 45a then transmits the examination purpose and the imaging plan that have been received, to the X-ray CT device 5 indicated by the machine model ID that has been received. When the processing circuitry of the X-ray CT device 5 receives the examination purpose and imaging plan, the processing circuitry causes the received examination purpose and imaging plan to be stored in association with each other, into the memory of the X-ray CT device 5. The examination purpose and imaging plan added to the imaging plan database 42a and the examination purpose and the imaging plan stored in the memory of the X-ray CT device 5 thereby become the same.

The modifying function 45b modifies an imaging plan. For example, the modifying function 45b receives an instruction to modify an imaging plan from a user via the input interface 43. The instruction to modify includes an imaging plan to be modified, a machine model ID corresponding to the imaging plan to be modified, an examination purpose corresponding to the imaging plan to be modified, and how to modify the imaging plan to be modified. On the basis of the instruction to modify, the modifying function

45b then modifies the imaging plan to be modified that has been registered in the imaging plan database 42a.

The modifying function 45b then transmits the instruction to modify, to the X-ray CT device 5 indicated by the machine model ID corresponding to the imaging plan to be modified, to modify the imaging plan to be modified that has been stored in the memory of the X-ray CT device 5. When the processing circuitry of the X-ray CT device 5 receives the instruction to modify, the processing circuitry modifies the imaging plan to be modified that has been stored in the memory of the X-ray CT device 5, according to the instruction to modify. The imaging plan to be modified that has been registered in the imaging plan database 42a and modified and the imaging plan to be modified that has been stored in the memory of the X-ray CT device 5 and modified thereby become the same.

As described above, the registered or modified imaging plans are synchronized with each other between the imaging plan database 42a of the terminal device 4 and the memory of the X-ray CT device 5. Therefore, the imaging plan database 42a has, registered therein, the most recent imaging plan for the X-ray CT device 5, for each examination purpose.

The registration and modification of an imaging plan are performed by a user operating the terminal device 4. For example, a user manages imaging plans according to functions of the X-ray CT device 5 and circumstances of the institution, such as a hospital 3 (for example, whether or not the institution regards image quality and/or reduction of radiation doses as important). For example, even if recommended imaging plans (imaging plans that are recommended) have already been stored in the X-ray CT device 5 at the time of shipment of the X-ray CT device 5, a user manages the imaging plans according to the functions of the X-ray CT device 5 and circumstances of the institution, for example, as described above. The user manages the imaging plans in a closed world that is the institution. That is, each institution has a user who manages imaging plans and the user manages the imaging plans for that institution.

Therefore, if the X-ray CT device 5 executes imaging by using, as is, an imaging plan registered or modified by a user and generates CT image data and image data, control of a radiation dose of X-rays received by a subject and control of image quality of the image data generated by the X-ray CT device 5 will depend on skills and experience of the user.

Furthermore, there are guidelines defining a recommended range of radiation doses, for example, for each examination purpose. However, even if a user manages imaging plans to comply with the guidelines, the user may sometimes be unable to adopt new guidelines promptly. For example, some users may not notice that new guidelines are available. Furthermore, some users may not promptly adapt the imaging plans to the new guidelines even if they have noticed that the new guidelines are available. In these cases, the imaging plans are not adapted to the new guidelines, and examinations will continue to be performed with the conventional radiation doses and image quality. Therefore, this will be detrimental to the interests of subjects. If a user's ability to notice availability of new guidelines and the user's ability to adapt imaging plans to the new guidelines when the user notices the availability of the new guidelines are regarded as skills of the user, imaging plans can again be said to be dependent on skills of users.

Therefore, the evaluation server 10 and the evaluation system 1 according to the first embodiment execute processes described below to enable generation of imaging plans not dependent on skills and experience of users. That is, the evaluation server 10 and the evaluation system 1 execute the following processes to enable generation of imaging plans that are more appropriate.

FIG. 4 is a diagram for explanation of an example of processing executed by the evaluation requesting function 45c according to the first embodiment. The evaluation requesting function 45c transmits an imaging plan 6 to be evaluated, a machine model ID 7, and an examination purpose 8, to the evaluation server 10, to cause the evaluation server 10 to evaluate the imaging plan 6. The imaging plan 6 is an example of a first imaging plan. An imaging condition included in the imagine plan 6 is an example of a first imaging condition. A reconstruction condition included in the imaging plan 6 is an example of a first reconstruction condition. A postprocessing condition included in the imaging plan 6 is an example of a first postprocessing condition.

For example, the evaluation requesting function 45c receives specification of the imaging plan 6 to be evaluated from a user via the input interface 43. For example, by operating the input interface 43, the user specifies the imaging plan 6 to be evaluated from all of imaging plans that have been registered in the imaging plan database 42a. The evaluation requesting function 45c then refers to the imaging plan database 42a to identify the machine model ID 7 and examination purpose 8 corresponding to the specified imaging plan 6 to be evaluated. The evaluation requesting function 45c then controls the communication interface 41 to transmit the specified imaging plan 6 to be evaluated and the identified machine model ID 7 and examination purpose 8, to the evaluation server 10. The communication interface 41 thereby transmits the imaging plan 6, the machine model ID 7, and the examination purpose 8 to the evaluation server 10 via the network 2. As described above, the evaluation requesting function 45c transmits the imaging plan 6 and so on when the specification of the imaging plan 6 to be evaluated is received from the user. Therefore, the evaluation requesting function 45c is able to transmit the imaging plan 6 and so on to the evaluation server 10 at any time.

The evaluation requesting function 45c may transmit plural imaging plans and so on to the evaluation server 10 if specification of plural imaging plans to be evaluated is received from a user. Furthermore, the evaluation requesting function 45c may automatically transmit the imaging plan 6 and so on to the evaluation server 10 at predetermined time intervals.

The display controlling function 45d and setting function 45e will be described later.

The evaluation server 10 evaluates the imaging plan 6 and generates an imaging plan not dependent on skills and experience of the user. The evaluation server 10 is implemented by, for example, a computer, such as a server. FIG. 5 is a diagram illustrating an example of a configuration of the evaluation server 10 according to the first embodiment. The evaluation server 10 includes a communication interface 11, a memory 12, an input interface 13, a display 14, and processing circuitry 15.

The communication interface 11 is connected to the processing circuitry 15 and controls communication between the evaluation server 10 and the terminal device 4. The communication interface 11 receives various data and information from the terminal device 4 and transmits the received data and information to the processing circuitry 15. For example, when the communication interface 11 receives the imaging plan 6, machine model ID 7, and examination purpose 8 transmitted from the terminal device 4, the communication interface 11 transmits the received imaging plan 6, machine model ID 7, and examination purpose 8, to the processing circuitry 15. When the processing circuitry 15 receives the imaging plan 6, machine model ID 7, and examination purpose 8 transmitted by the communication interface 11, the processing circuitry 15 stores the received imaging plan 6, machine model ID 7, and examination purpose 8, into the memory 12. The imaging plan 6, machine model ID 7, and examination purpose 8 are thereby able to be used in various processes described below. Furthermore, the communication interface 11 transmits various data and information to the terminal device 4. For example, the communication interface 11 is implemented by a network card, a network adapter, or an NIC.

The memory 12 is connected to the processing circuitry 15 and stores various data and information. For example, the memory 12 stores a guideline database 12a and a performance information database 12b.

The guideline database 12a has, registered therein, for each examination purpose, a range of radiation doses that is a range of radiation doses of X-days received by a subject and recommended in various guidelines. Examples of this range of radiation doses include a range defined by an upper limit value and a lower limit value of radiation doses or a range defined by just an upper limit value of radiation doses. FIG. 6 is a diagram illustrating an example of a data structure of the guideline database 12a according to the first embodiment. As illustrated in FIG. 6, the guideline database 12a has, registered therein, plural records each having an item, "Examination Purpose", and an item, "Range of Radiation Doses".

For the item, "Examination Purpose", the examination purpose is registered. For the item, "Range of Radiation Doses", the range of radiation doses corresponding to the examination purpose and recommended in various guidelines is registered. The range of radiation doses registered in the guideline database 12a is based on various guidelines indicating recommended ranges of radiation doses, such as "Diagnostic Reference Levels" and "Guidelines for Medical Exposures", for example. Furthermore, the guideline database 12a has, registered therein, the most recent ranges of radiation doses based on the most recent guidelines. The registered content of the guideline database 12a is used in the processes described below. Accordingly, the ranges of radiation doses recommended in various guidelines are stored in the memory 12 in the form that is able to be used by a computer.

The performance information database 12b has, registered therein, for each of types of the X-ray CT devices 5, performance information (the most recent performance information) related to the most recent performance of the X-ray CT devices 5 to be managed. FIG. 7 is a diagram illustrating an example of a data structure of the performance information database 12b according to the first embodiment. As illustrated in FIG. 7, the performance information database 12b has, registered therein, plural records each having an item, "Machine Model ID", and an item, "Performance Information".

For the item, "Machine Model ID", the machine model ID of the X-ray CT device 5 to be managed is registered. For the item, "Performance Information", the most recent performance information on the X-ray CT device 5 indicated by the machine model ID is registered. For example, the performance information includes: the maximum number of rows of X-ray detecting elements that are able to be used by the X-ray detector included in the X-ray CT device 5; the maximum rotating speed of the rotating frame included in the X-ray CT device 5; the maximum value of tube voltage that is able to be used by the X-ray CT device 5; the maximum value of tube current that is able to be used by the X-ray CT device 5; the type of an imaging mode that is able to be used by the X-ray CT device 5; information (AEC information) indicating whether or not the X-ray CT device 5 is capable of performing AEC; a type of reconstruction processing that is able to be used by the X-ray CT device 5; and a type of postprocessing that is able to be used by the X-ray CT device 5.

That is, the performance information includes imaging conditions, a reconstruction condition, and a postprocessing condition that are able to be used by the X-ray CT device 5. Specifically, the maximum number of rows of X-ray detecting elements, the maximum rotating speed, the maximum value of tube voltage, the maximum value of tube current, the type of an imaging mode, and the AEC information are the imaging conditions included in the performance information. Furthermore, the type of reconstruction processing that is able to be used by the X-ray CT device 5 is the reconstruction condition included in the performance information. The type of postprocessing that is able to be used by the X-ray CT device 5 is the postprocessing condition included in the performance information.

The imaging conditions included in the performance information are an example of second imaging conditions. The reconstruction condition included in the performance information is an example of a second reconstruction condition. The postprocessing condition included in the performance information is an example of a second postprocessing condition.

The registered content of the performance information database 12b is used in the processes described below. Accordingly, the performance information of the X-ray CT device 5 is stored in the memory 12 in the form that is able to be used by a computer.

As described above, the guideline database 12a has, registered therein, the most recent ranges of radiation doses based on the most recent guidelines. The performance information database 12b also has, registered therein, the most recent performance information on the X-ray CT devices 5 to be managed. The following description is on an example of a procedure in which such most recent ranges of radiation doses and most recent performance information are registered.

For example, an external server may transmit, when a guideline with which a recommended range of radiation doses that has been newly prescribed is registered is formulated, that most recent recommended range of radiation doses registered with the guideline, to the evaluation server 10. For example, this external server transmits the most recent recommended range of radiation doses and an examination purpose corresponding to the most recent recommended range of radiation doses in association with each other, to the evaluation server 10. The evaluation server 10 receives the most recent recommended range of radiation doses and examination purpose transmitted by the external server. By using the most recent recommended range of radiation doses and examination purpose received, the processing circuitry 15 of the evaluation server 10 updates a range of radiation doses that has been registered in the guideline database 12a with the most recent recommended range of radiation doses. For example, the processing circuitry 15 identifies a record having the received examination purpose registered for the item, "Examination Purpose", from all of the records that have been registered in the guideline database 12a. The processing circuitry 15 then rewrites the range of radiation doses registered for the item, "Range of Radiation Doses", of the identified record, to the received most recent recommended range of radiation doses.

Furthermore, for example, an external server may transmit the most recent imaging condition, the most recent reconstruction condition, or the most recent postprocessing condition that is able to be used by the X-ray CT device 5, to the evaluation server 10. For example, this external server transmits the most recent imaging condition, the most recent reconstruction condition, or the most recent postprocessing condition that is able to be used by the X-ray CT device 5, and the machine model ID, in association with each other, to the evaluation server 10. The evaluation server 10 receives the most recent imaging condition, most recent reconstruction condition, or most recent postprocessing condition and machine model ID transmitted by the external server. By using the most recent imaging condition, most recent reconstruction condition, or most recent postprocessing condition, and machine model ID received, the processing circuitry 15 updates performance information that has been registered in the performance information database 12b with the most recent performance information. For example, the processing circuitry 15 identifies a record having the received machine model ID registered for the item, "Machine Model ID", from all of the records that have been registered in the performance information database 12b. The processing circuitry 15 then rewrites the imaging condition, reconstruction condition, or postprocessing condition included in the performance information registered for the item, "Performance Information", of the identified record, to the received most recent imaging condition, most recent reconstruction condition, or most recent postprocessing condition.

Such update of the content registered in the guideline database 12a and performance information database 12b with the most recent content results in constant registration of the most recent content in the guideline database 12a and performance information database 12b. As a result, the evaluation server 10 according to the first embodiment performs evaluation on the basis of the most recent content and transmits a result of the evaluation based on the most recent content, to the terminal device 4.

The memory 12 stores a subject model that is a model of subjects to be used in the processes described below. The memory 12 also stores programs for the processing circuitry 15 to implement various functions. For example, the memory 12 is implemented by, for example, a semiconductor memory device, such as a flash memory, a hard disk, or an optical disk. The memory 12 is an example of a storage unit.

The input interface 13 is connected to the processing circuitry 15 and receives input operations for various instructions, requests, and information from a user. For example, the input interface 13 converts an input operation received from a user into an electric signal and transmits the electric signal to the processing circuitry 15. The input interface 13 is implemented by, for example, a trackball, a switch button, a mouse, a keyboard, a touchpad by which an input operation is executed through a touch on an operation surface, a touch screen having a display screen and a touchpad that are integrated with each other, a contactless input circuit using an optical sensor, and a voice input circuit. In this specification, the input interface 13 is not necessarily an input interface having physical operation parts, such as a mouse and a keyboard. For example, examples of the input interface 13 include electric signal processing circuitry that receives an electric signal corresponding to an input operation from an external input device provided separately from the device and transmits this electric signal to the processing circuitry 15.

The display 14 is connected to the processing circuitry 15 and displays various types of information and images. For example, the display 14 converts information and data transmitted from the processing circuitry 15 into electric signals for display and outputs the electric signals. The display 14 is implemented by, for example, a liquid crystal monitor, a CRT monitor, or a touch panel.

The processing circuitry 15 controls operation of the evaluation server 10 according to an input operation received from a user via the input interface 13. For example, the processing circuitry 15 is implemented by a processor. The processing circuitry 15 executes an evaluating function 15a, a generating function 15b, and a transmitting function 15c. The evaluating function 15a is an example of an evaluating unit. The generating function 15b is an example of a generating unit. The transmitting function 15c is an example of an output unit.

Processing functions that the processing circuitry 15 has are each stored, for example, in the form of a program that is able to be executed by a computer, into the memory 12. That is, processing functions including the evaluating function 15a, the generating function 15b, and the transmitting function 15c that are components of the processing circuitry 15 illustrated in FIG. 5 are stored in the memory 12, in the form of programs that are able to be executed by a computer. The processing circuitry 15 implements the functions respectively corresponding to the programs by reading the programs from the memory 12 and executing the read programs. In other words, the processing circuitry 15 that has read the programs has the functions illustrated in the processing circuitry 15 of FIG. 5.

The evaluating function 15a makes an evaluation of the imaging plan 6 transmitted from the terminal device 4 and transmits a result of the evaluation to the terminal device 4. The evaluating function 15a makes an evaluation of the imaging plan 6 with respect to the radiation dose, on the basis of the imaging plan 6, a range of radiation doses registered in the guideline database 12a, and performance information registered in the performance information database 12b. For example, the evaluating function 15a evaluates whether or not the radiation dose based on the imaging plan 6 is an adequate radiation dose. In a specific example, the evaluating function 15a evaluates whether or not the radiation dose based on the imaging plan 6 is in a recommended range of radiation doses. A radiation dose of X-rays received by a subject is an example of an evaluation item. A recommended range of radiation doses is an example of numerical information related to an evaluation item, the numerical information conforming to guidelines related to the imaging plan 6. The following description is related to a case where the number of evaluation items is one (a radiation dose of X-rays), but the number of evaluation items may be plural. That is, the number of evaluation items may be at least one.

The generating function 15b generates an imaging plan 50 that has been improved, by changing (modifying) the imaging plan 6 to reduce the radiation dose therein. The imaging plan 50 is an example of a second imaging plan.

The transmitting function 15c transmits the imaging plan 50 and a result of the evaluation, to the terminal device 4.

Figure 8B:
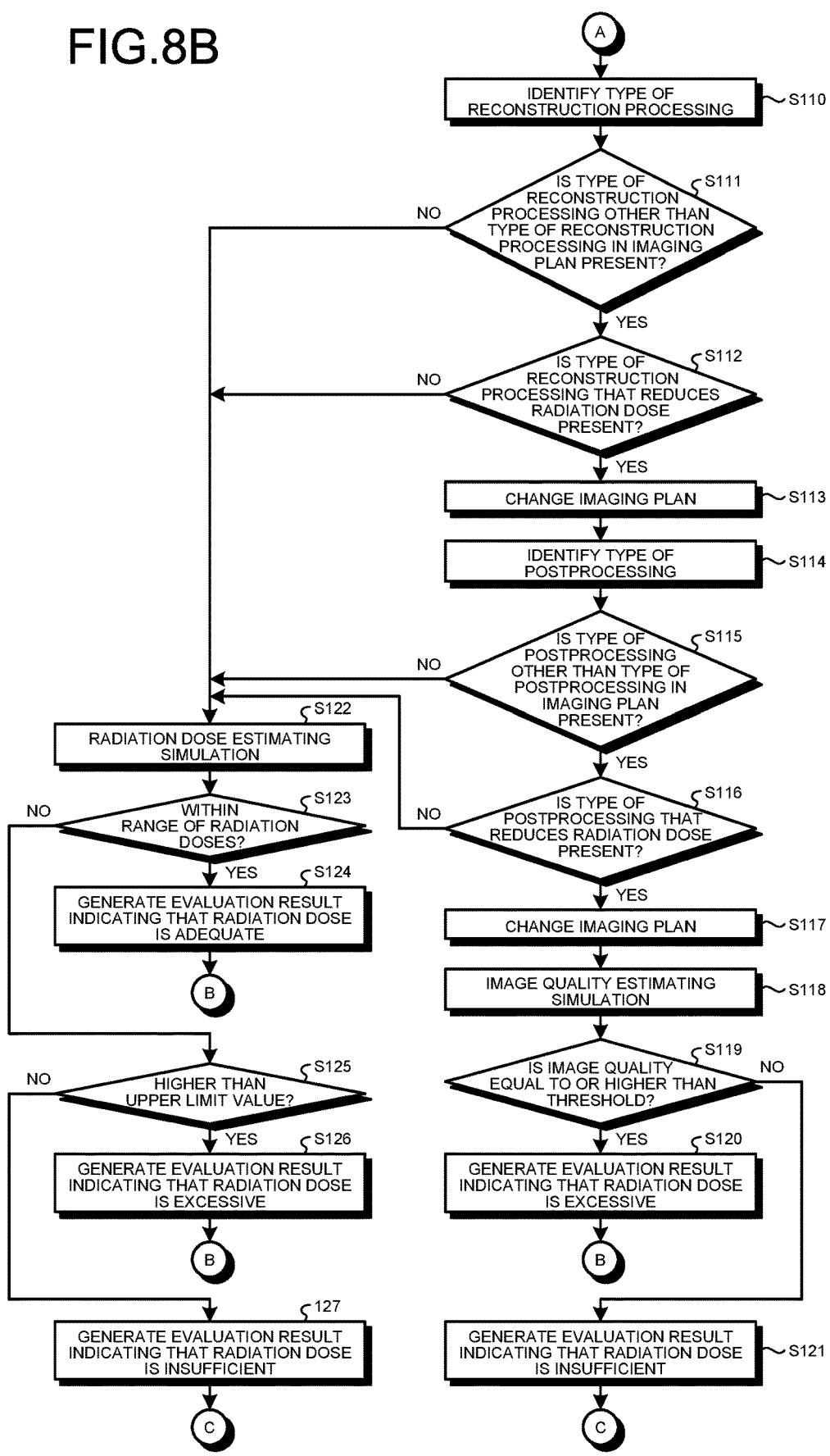
FIG. 8B is a flowchart illustrating an example of a flow of a process executed by the evaluation server according to the first embodiment.
Figure 8C:
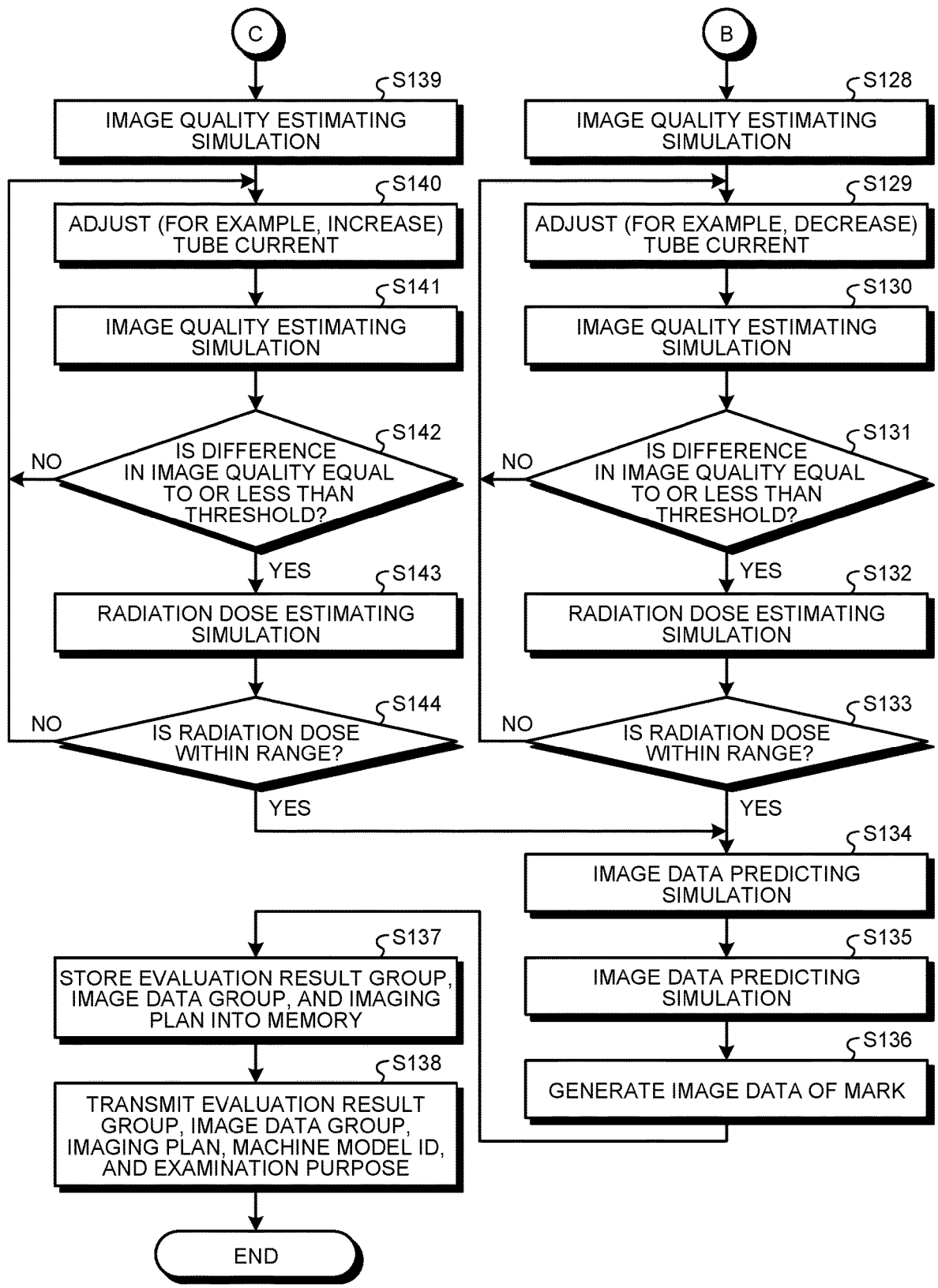
FIG. 8C is a flowchart illustrating an example of a flow of a process executed by the evaluation server according to the first embodiment.

FIG. 8A, FIG. 8B, and FIG. 8C are flowcharts each illustrating an example of a flow of a process executed by the evaluation server 10 according to the first embodiment. The processes illustrated in FIG. 8A, FIG. 8B, and FIG. 8C are executed when, for example, the evaluating function 15a of the processing circuitry 15 in the evaluation server 10 receives the imaging plan 6, the machine model ID 7, and the examination purpose 8 transmitted by the terminal device 4.

As illustrated in FIG. 8A, the generating function 15b generates an imaging plan 50 that is a copy of the imaging plan 6 and stores the imaging plan 50 into the memory 12 (Step S101). The imaging plan 50 is digital data that are the same as those of the imaging plan 6. The imaging plan 50 is improved by various processes described later and finally transmitted to the terminal device 4.

The evaluating function 15a then acquires performance information corresponding to the machine model ID 7, from the performance information database 12b having the most recent performance information registered therein (Step S102). The evaluating function 15a then identifies the number of rows of X-ray detecting elements and imaging modes that are included in the performance information acquired (Step S103). The identified number of rows of X-ray detecting elements is the maximum number of rows of X-ray detecting elements that are able to be used by the X-ray detector included in the X-ray CT device 5 indicated by the machine model ID 7. The identified types of imaging modes are types of imaging modes that are able to be used by the X-ray CT device 5 indicated by the machine model ID 7. A case where the number of rows of X-ray detecting elements identified at Step S103 is "80" and the types of imaging modes identified at Step S103 include "helical scan" and "conventional scan" will be described below as an example.

The evaluating function 15a then determines whether or not the number of rows of detecting elements identified at Step S103 is larger than the number of rows of X-ray detecting elements included in the imaging plan 6 (Step S104). A case where the number of rows of X-ray detecting elements included in the imaging plan 6 is "16" will be described below as an example. In this case, for example, it is considered that although the X-ray CT device 5 is capable of using 80 rows of X-ray detecting elements, the X-ray CT device 5 uses only 16 rows of X-ray detecting elements. In this case, at Step S104, the evaluating function 15a determines that "80", the identified number of rows of the detecting elements, is larger than "16", the number of rows of X-ray detecting elements included in the imaging plan 6.

If the evaluating function 15a has determined that the number of rows of the detecting elements identified at Step S103 is equal to or less than the number of rows of X-ray detecting elements included in the imaging plan 6 (Step S104: No), the evaluating function 15a proceeds to Step S107.

On the contrary, if the evaluating function 15a has determined that the number of rows of the detecting elements identified at Step S103 is larger than the number of rows of X-ray detecting elements included in the imaging plan 6 (Step S104: Yes), the evaluating function 15a proceeds to Step S105.

The evaluating function 15a determines whether or not any type of an imaging mode with a radiation dose less than that of the type of the imaging mode included in the imaging plan 6 is present in the types of imaging modes identified at Step S103 (Step S105). A case where the type of the imaging mode included in the imaging plan 6 is "helical scan" will be described below as an example.

The X-ray CT device 5 is able to reduce the radiation dose if the X-ray CT device 5 sets, as an imaging condition, the number of rows larger than the number of rows of X-ray detecting elements included in the imaging plan 6 and changes the imaging mode from "helical scan" to "conventional scan". This is due to the following reasons. For example, in "helical scan", X-rays emitted to a subject overlap one another in a large part of the subject. In contrast, in "conventional scan" using a larger number of rows of X-ray detecting elements, X-rays emitted to the subject overlap one another in a smaller part of the subject than in "helical scan". In "conventional scan" using the larger number of rows of X-ray detecting elements, use efficiency of X-rays is high. Therefore, the X-ray CT device 5 is able to reduce the radiation dose.

Accordingly, for example, at Step S105, the evaluating function 15a determines that "conventional scan", the imaging mode with a lower radiation dose than "helical scan", the imaging mode included in the imaging plan 6, is present in "helical scan" and "conventional scan" included in the types of imaging modes identified at Step S103.

If the evaluating function 15a determines that no imaging mode with a lower radiation dose than the imaging mode included in the imaging plan 6 is present in the types of imaging modes identified at Step S103 (Step S105: No), the evaluating function 15a proceeds to Step S107.

On the contrary, if the evaluating function 15a determines that any imaging mode with a lower radiation dose than the imaging mode included in the imaging plan 6 is present in the types of imaging modes identified at Step S103 (Step S105: Yes), the evaluating function 15a proceeds to Step S106.

The generating function 15b changes the number of rows of X-ray detecting elements and imaging mode that are included in the imaging plan 50 to the number of rows of X-ray detecting elements identified at Step S103 and the imaging mode with the lower radiation dose determined to be present at Step S105 (Step S106). Accordingly, at Step S106, the generating function 15b modifies the imaging plan 50 to reduce the radiation dose.

The evaluating function 15a then identifies a rotating speed included in the performance information that has been acquired (Step S107). The rotating speed identified is the maximum rotating speed of the rotating frame included in the X-ray CT device 5 indicated by the machine model ID 7. A case where the rotating speed identified at Step S107 is "0.5" seconds/turn will be described below as an example.

The evaluating function 15a then determines whether or not the rotating speed identified at Step S107 is higher than the rotating speed included in the imaging plan 6 (Step S108). A case where the rotating speed included in the imaging plan 6 is "1.0" seconds/turn will be described below as an example. In this case, although the maximum rotating speed of the rotating frame of the X-ray CT device 5 indicated by the machine model ID 7 is "0.5" seconds/turn, the rotating speed of "1.0" seconds/turn has been set as an imaging condition in the imaging plan 6. At Step S108, the evaluating function 15a thus determines that "0.5" seconds/turn, the identified rotating speed, is higher than "1.0" seconds/turn, the rotating speed included in the imaging plan 6.

If the evaluating function 15a has determines that the rotating speed identified at Step S107 is equal to or less than the rotating speed included in the imaging plan 6 (Step S108: No), the evaluating function 15a proceeds to Step S110.

On the contrary, if the evaluating function 15a has determined that the rotating speed identified at Step S107 is higher than the rotating speed included in the imaging plan 6 (Step S108: Yes), the evaluating function 15a proceeds to Step S109.

The generating function 15b changes the rotating speed included in the imaging plan 50 to the rotating speed identified at Step S107 (Step S109). As the rotating speed is increased, the time over which the subject is irradiated with X-rays is decreased and the radiation dose is thus reduced. Therefore, at Step S109, the generating function 15b modifies the imaging plan 50 to reduce the radiation dose.

At Step S109, the generating function 15b modifies the time information included in the imaging plan 50, in association with the reduction in imaging time.

At Steps S106 and S109 described above, the generating function 15b generates the imaging plan 50 by changing the imaging condition included in the copy (the imaging plan 50) of the imaging plan 6 to any imaging condition not used by the X-ray CT device 5, if that imaging condition that is not used by the X-ray CT device 5 even though using that imaging condition enables reduction of the radiation dose is present in the imaging conditions included in the performance information. That is, the generating function 15b generates the imaging plan 50 by changing the imaging condition included in the imaging plan 50 to the imaging condition that enables reduction of the radiation dose.

As illustrated in FIG. 8B, the evaluating function 15a then identifies types of reconstruction processing included in the performance information that has been acquired (Step S110). The identified types of reconstruction processing are the types of reconstruction processing that are able to be used by the X-ray CT device 5 indicated by the machine model ID 7. A case where the identified types of reconstruction processing are three types, "A", "B", and "C", will be described below as an example.

The evaluating function 15a then determines whether or not any type of reconstruction processing other than the type of reconstruction processing included in the imaging plan 6 is present in the types of reconstruction processing identified at Step S110 (Step S111). A case where the type of reconstruction processing included in the imaging plan 6 is "A" will be described below as an example. In this case, at Step S111, the evaluating function 15a determines that "B" and "C", the types of reconstruction processing other than "A", the type of reconstruction processing included in the imaging plan 6", are present in A", "B", and "C", the types of reconstruction processing that are able to be used by the X-ray CT device 5.

If the evaluating function 15a has determined that no type of reconstruction processing other than the type of reconstruction processing included in the imaging plan 6 is present (Step S111: No), the evaluating function 15a proceeds to Step S122.

On the contrary, if the evaluating function 15a has determined that any type of reconstruction processing other than the type of reconstruction processing included in the imaging plan 6 is present (Step S111: Yes), the evaluating function 15a performs the following processing. For example, the evaluating function 15a determines whether or not any type of reconstruction processing that enables reduction of the radiation dose of X-rays received by a subject as compared to the type of reconstruction processing included in the imaging plan 6 is present in the types of reconstruction processing determined to be present at Step S111 (Step S112).

It will hereinafter be assumed that the image quality of the CT image data is improved when reconstruction processing of the type, "C", is used, as compared to when reconstruction processing of the type, "A", is used, in a case where images are reconstructed on the basis of the same raw data (projection data). That is, an image is able to be generated on the basis of raw data collected using X-rays of a comparative low radiation dose when reconstruction processing of the type, "C", is used, the image being equivalent to an image acquired by reconstruction processing of the type, "A", on raw data collected using X-rays of a comparatively high radiation dose. Therefore, it is supposed herein that using reconstruction processing of the type, "C", enables reduction of the radiation dose of X-rays received by a subject. In this case, at Step S112, the evaluating function 15a determines "C", the type of reconstruction processing enabling reduction of the radiation dose of X-rays received by a subject, is present.

The following description relates to the processing at Step S111 and Step S112. Results of the determinations at Steps S111 and S112 each being a yes means that the X-ray CT device 5 does not use reconstruction processing of the type, "C", even though reconstruction processing of the type, "C", is usable. That is, results of the determinations at Steps S111 and S112 each being a yes means that the reconstruction processing condition has not been set appropriately even though the X-ray CT device 5 is capable of performing imaging at a lower radiation dose. This may happen, for example, in a case where a user does not know that reconstruction processing of the type, "C", is available even though reconstruction processing of the type, C", that enables reduction of radiation doses has become newly available. Therefore, if the user does not know the availability of reconstruction processing of the type, "C", reconstruction processing of the type, "C", would not be installed in the X-ray CT device 5. The X-ray CT device 5 would thus be unable to use reconstruction processing of the type, "C".

Furthermore, the X-ray CT device 5 does not use reconstruction processing of the type, "C", even though the radiation dose is able to be reduced when reconstruction processing of the type, "C", is used. Because reconstruction processing of the type, "C", is not used, the imaging conditions included in the imaging plan 6 are set such that the radiation dose would be higher than that in a case where reconstruction processing of the type, "C", is used. Therefore, if results of the determinations at Steps S111 and S112 are each a yes, the imaging conditions have not been appropriately set even though the X-ray CT device 5 is capable of reconstructing CT image data having image quality required for diagnosis with a smaller radiation dose.

If the evaluating function 15a determines that no type of reconstruction processing that enables reduction of the radiation dose of X-rays received by a subject is present (Step S112: No), the evaluating function 15a proceeds to Step S122.

On the contrary, if the evaluating function 15a determines that any type of reconstruction processing that enables reduction of the radiation dose of X-rays received by a subject is present (Step S112: Yes), the evaluating function 15a proceeds to Step S113.

The generating function 15b changes the type of reconstruction processing included in the imaging plan 50 to the type of reconstruction processing that enables reduction of the radiation dose of X-rays received by a subject (Step S113). The generating function 15b thus modifies the imaging plan 50 at Step S113 such that the radiation dose is able to be reduced.

At Step S113, the generating function 15b generates the imaging plan 50 by changing the reconstruction condition included in the copy (the imaging plan 50) of the imaging plan 6 to any reconstruction condition not used by the X-ray CT device 5, if that reconstruction condition that is not used by the X-ray CT device 5 even though using that reconstruction condition enables reduction of the radiation dose is present in the reconstruction conditions included in the performance information.

The evaluating function 15a then identifies the types of postprocessing included in the performance information that has been acquired (Step S114). The identified types of postprocessing are types of postprocessing that are able to be used by the X-ray CT device 5 indicated by the machine model ID 7. A case where the types of postprocessing identified are three types, "D", "E", and "F", will be described below as an example.

The evaluating function 15a determines whether or not any type of postprocessing other than the type of postprocessing included in the imaging plan 6 is present in the types of postprocessing identified at Step S114 (Step S115). A case where the type of postprocessing included in the imaging plan 6 is "D" will be described below as an example. In this case, at Step S115, the evaluating function 15a determines that the types of postprocessing, "E" and "F", other than the type of postprocessing, "D", included in the imaging plan 6 are present in the types of postprocessing, "D", "E", and "F", that are able to be used by the X-ray CT device 5.

If the evaluating function 15a has determined that no type of postprocessing other than the type of postprocessing included in the imaging plan 6 is present (Step S115: No), the evaluating function 15a proceeds to Step S122.

On the contrary, if the evaluating function 15a has determined that any type of postprocessing other than the type of postprocessing included in the imaging plan 6 is present (Step S115: Yes), the evaluating function 15a executes the following processing. For example, the evaluating function 15a determines whether or not any type of postprocessing that enables reduction of the radiation dose of X-rays received by a subject as compared to the type of postprocessing included in the imaging plan 6 is present in the types of postprocessing determined to be present at Step S115 (Step S116).

It will hereinafter be assumed that image quality of image data is improved when postprocessing of the type, "F", is used in postprocessing CT image data, as compared to when postprocessing of the type, "D", is used in postprocessing the same CT image data. That is, when postprocessing of the type, "F", is used, image data are able to be generated on the basis of CT image data collected using X-rays of a comparatively low radiation dose, the image data being equivalent to image data acquired by subjecting CT image data collected using X-rays of a comparatively high radiation dose to postprocessing of the type, "D". Therefore, it is supposed herein that using postprocessing of the type, "F", enables reduction of the radiation dose of X-rays received by a subject. In this case, at Step S116, the evaluating function 15a determines that "F", the type of postprocessing enabling reduction of the radiation dose of X-rays received by a subject is present.

The following description relates to the processing at Step S115 and Step S116. Results of the determinations at Steps S115 and S116 each being a yes means that postprocessing of the type, "F", is not used even though the X-ray CT device 5 is capable of using postprocessing of the type, "F". That is, results of the determinations at Steps S115 and S116 each being a yes means that the postprocessing conditions have not been appropriately set even though the X-ray CT device 5 is capable of performing imaging at a lower radiation dose. This may happen if, for example, a user does not know that postprocessing of the type, "F", is available even though postprocessing of the type, F'", that enables reduction of a radiation dose has become newly available.

Furthermore, the X-ray CT device 5 does not use postprocessing of the type, "F", even though using postprocessing of the type, "F", enables reduction of a radiation dose. Because postprocessing of the type, F", has not been used, the imaging conditions included in the imaging plan 6 have been set such that the radiation dose becomes higher, as compared to a case where postprocessing of the type, "F", is used. Therefore, results of the determinations at Steps S115 and S116 each being a yes means that the imaging conditions have not been appropriately set even though the X-ray CT device 5 is capable of generating image data having image quality required for diagnosis with a smaller radiation dose.

If the evaluating function 15a has determined that there is no type of postprocessing that enables reduction of the radiation dose of X-rays received by a subject (Step S116: No), the evaluating function 15a proceeds to Step S122.

On the contrary, if the evaluating function 15a determines that any type of postprocessing that enables reduction of the radiation dose of X-rays received by a subject is present (Step S116: Yes), the evaluating function 15a proceeds to Step S117.

The generating function 15b changes the type of postprocessing included in the imaging plan 50 to the type of postprocessing that enables reduction of the radiation dose of X-rays received by a subject (Step S117). The generating function 15b thus modifies the imaging plan 50 at Step S117 such that the radiation dose is able to be reduced.

At Step S117, in a case where any postprocessing condition that is not used by the X-ray CT device 5 even though using the postprocessing condition enables reduction of a radiation dose is present in the postprocessing conditions included in the performance information, the generating function 15b generates the imaging plan 50 by changing the postprocessing condition included in the copy (the imaging plan 50) of the imaging plan 6 to the postprocessing condition not used by the X-ray CT device 5.

The processing at Steps S114 to S117 may be omitted. Furthermore, the processing at Steps S110 to S113 may be omitted. For example, in a case where the processing at Steps S110 to S113 is performed, the processing at Steps S114 to S117 may be omitted. Furthermore, for example, in a case where the processing at Steps S114 to S117 is performed, the processing at Steps S110 to S113 may be omitted.

On the basis of the imaging plan 50, the machine model ID 7, and the examination purpose 8, the evaluating function 15a then executes an image quality estimating simulation (Step S118). The image quality estimating simulation executed at Step S118 is a simulation for estimating image quality of image data generated. In this simulation, the X-ray CT device 5 indicated by the machine model ID 7 performs imaging of a subject indicated by a subject model under imaging conditions included in the imaging plan 50, the imaging fulfilling the examination purpose 8. The X-ray CT device 5 then generates CT image data on the basis of reconstruction conditions included in the imaging plan 50 and generates the image data from the CT image data on the basis of postprocessing conditions included in the imaging plan 50. The subject model has been stored in the memory 12, and the evaluating function 15a acquires the subject model from the memory 12 and uses the subject model when executing the image quality estimating simulation. Image quality based on the imaging plan 50 is estimated in the image quality estimating simulation at Step S118. The image quality includes, for example, at least one of a standard deviation (SD) and a contrast to noise ratio (CNR).

The evaluating function 15a then determines whether or not the image quality estimated by the image quality estimating simulation at Step S118 is equal to or greater than a predetermined threshold (predetermined image quality) (Step S119).

If it has been determined that the estimated image quality is equal to or greater than the predetermined threshold (Step S119: Yes), it is considered that the imaging plan 6 has not been set appropriately even though image data having high image quality equal to or greater than the predetermined threshold are able to be generated and thus that there is room for reduction in the radiation dose. In this case, it is also considered that the imaging plan 6 needs to be improved.

As described above, at Steps S118 and S119, the evaluating function 15a estimates image quality of image data acquired through imaging by the X-ray CT device 5 using the imaging plan 50, when there is any reconstruction condition that is not used by the X-ray CT device 5 even through the reconstruction condition enables reduction of a radiation dose. If the estimated image quality is equal to or higher than the threshold, the evaluating function 15a determines that the radiation dose of X-rays received by a subject is higher the range of radiation doses stored in the memory 12.

Therefore, in this case (Step S119: Yes), the generating function 15b generates an evaluation result, "Improvement Needed (Excess Radiation Dose)", to be displayed on the display 14 (Step S120). The evaluation result, "Improvement Needed (Excess Radiation Dose)", indicates that the imaging plan 6 needs to be improved and that there is room for reduction in the radiation dose. The generating function 15b then proceeds to Step S128.

At Step S120, the generating function 15b may generate, as an evaluation result, a score or an achievement rate. For example a case where an SD of an image has been estimated as image quality at Step S118 will be described as an example. A case where the generating function 15b generates a score as an evaluation result will be described first. For example, the generating function 15b firstly determines whether or not the estimated SD is included in a range (a first range) of "Target SD−α" or more and "Target SD+α" or less. A target SD is an SD that is targeted. Furthermore, a is a predetermined value that is positive.

If the estimated SD is included in the first range, the generating function 15b generates a score S1 that is comparatively high. On the contrary, if the estimated SD is not included in the first range, the generating function 15b determines whether or not the estimated SD is included in any one of: a range (a second range) of "Target SD−α−β" or more and less than "Target SD−α"; and a range (a third range) of "Target SD+α+β" or less and larger than "Target SD+α". If the estimated SD is included in any one of the second range and third range, the generating function 15b generates a score S2 that is midrange and lower than the score S1.

On the contrary, if the estimated SD is not included in any of the second range and third range, the generating function 15b generates a score S3 that is comparatively low. The score S3 is a score lower than the score S2.

A case where the generating function 15b generates an achievement rate as an evaluation result will be described next. For example, the generating function 15b firstly calculates "Estimated SD/Target SD" that is a value resulting from division of the estimated SD by the target SD. If "Estimated SD/Target SD" is included in a range (a fourth range) of "0.95" or more and "1.05" or less, the generating function 15b then generates an achievement rate A1 that is comparatively high.

If "Estimated SD/Target SD" is included in any one of a range of "0.90" or more and less than "0.95" and a range of larger than "1.05" and "1.10" or less, the generating function 15b generates an achievement rate A2 that is midrange and lower than the achievement rate A1.

Furthermore, if "Estimated SD/Target SD" is less than "0.90" or larger than "1.10", the generating function 15b generates an achievement rate A3 that is comparatively low. This achievement rate A3 is an achievement rate lower than the achievement rate A2.

On the contrary, in a case where the estimated image quality has been determined to be less than the predetermined threshold (Step S119: No), it is considered that the image quality would become less than the predetermined threshold because the radiation dose is too low even if the reconstruction condition and the postprocessing condition that enable generation of CT image data of higher image quality and image data of higher image quality are set. That is, it is considered that a subject would be exposed to radiation even though useful information for diagnosis is unable to be acquired from image data generated by the X-ray CT device 5. In this case, it is also considered that the imaging plan 6 needs to be improved.

If the estimated image quality is less than the threshold (Step S119: No), the evaluating function 15a determines that the radiation dose of X-rays received by a subject is less than the range of radiation doses that has been stored in the memory 12.

Therefore, in this case, the generating function 15b generates an evaluation result, "Improvement Needed (Insufficient Radiation Dose)" to be displayed on the display (Step S121). This evaluation result, "Improvement Needed (Insufficient Radiation Dose)", indicates that the imaging plan 6 needs to be improved and the radiation dose is insufficient for acquisition of information useful for diagnosis. The generating function 15b then proceeds to Step S139.

If a result of the determination at any one of Step S111, Step S112, Step S115, and Step S116 is a no, the evaluating function 15a executes a radiation dose estimating simulation (Step S122).

This radiation dose estimating simulation is a simulation for estimating a radiation dose of X-rays received by a subject indicated by a subject model when the X-ray CT device 5 indicated by the machine model ID 7 performs imaging fulfilling the examination purpose 8 for the subject indicated by the subject model under the imaging conditions included in the imaging plan 6. By executing the radiation dose estimating simulation, the evaluating function 15a estimates a radiation dose based on the imaging plan 6.

The evaluating function 15a then determines whether or not the radiation dose estimated by the radiation dose estimating simulation at Step S122 is in the range of radiation doses that has been registered in the guideline database 12a (Step S123). For example, the evaluating function 15a acquires the range of radiation doses corresponding to the examination purpose 8, from the guideline database 12a. The evaluating function 15a then determines whether or not the radiation dose estimated by the radiation dose estimating simulation is in the range of radiation doses acquired.

If the estimated radiation dose is in the range of radiation doses (Step S123: Yes), the radiation dose of X-rays received by a subject is considered to be adequate.

At Step S122 described above, the evaluating function 15a estimates the radiation dose for the case where the X-ray CT device 5 performs imaging by using the imaging plan 6. If the estimated radiation dose is in the range of radiation doses stored in the memory 12 (Step S123: Yes), the evaluating function 15a determines that the radiation dose of X-rays received by a subject is in the range of radiation doses stored in the memory 12.

If the estimated radiation dose is in the range of radiation doses (Step S123: Yes), the generating function 15b generates an evaluation result, "Adequate Radiation Dose", to be displayed on the display 14 (Step S124). The evaluation result, "Adequate Radiation Dose", indicates that the radiation dose is adequate. The generating function 15b then proceeds to Step S128.

If the estimated radiation dose is not in the range of radiation doses, that is, if the estimated radiation dose is outside the range of radiation doses, it is considered that the radiation dose of X-rays received by a subject is not adequate and the imaging plan 6 needs to be improved. Therefore, if the estimated radiation dose is outside the range of radiation doses stored in the memory 12 (Step S123: Yes), the evaluating function 15a determines that the radiation dose of X-rays received by a subject is outside the range of radiation doses stored in the memory 12.

If the estimated radiation dose is not in the range of radiation doses (Step S123: No), the evaluating function 15a determines whether or not the estimated radiation dose is higher than the upper limit value of the range of radiation doses (Step S125). If the estimated radiation dose is higher than the upper limit value of the range of radiation doses (Step S125: Yes), it is considered that the radiation dose of X-rays received by a subject is larger than the recommended range of radiation doses. Therefore, in this case (Step S125: Yes), the generating function 15b generates an evaluation result, "Improvement Needed (Excess Radiation Dose)", to be displayed on the display 14 (Step S126). The generating function 15b then proceeds to Step S128.

On the contrary, if the estimated radiation dose is not higher than the upper limit value of the range of radiation doses (Step S125: No), that is, if the estimated radiation dose is less than the lower limit value of the range of radiation doses, it is considered that a subject would be exposed to radiation even though information useful for diagnosis would be unable to be obtained from image data generated by the X-ray CT device 5. In this case, it is considered that the subject would be needlessly exposed to radiation. Therefore, in this case (Step S125: No), the generating function 15b generates an evaluation result, "Improvement Needed (Insufficient Radiation Dose)", to be displayed on the display 14 (Step S127). The generating function 15b then proceeds to Step S139.

As illustrated in FIG. 8C, on the basis of the imaging plan 6, the machine model ID 7, and the examination purpose 8, the evaluating function 15a executes an image quality estimating simulation for estimating image quality based on the imaging plan 6 (Step S128).

The image quality estimating simulation executed at Step S128 is a simulation for estimating image quality of image data generated. In this simulation, the X-ray CT device 5 indicated by the machine model ID 7 performs imaging of a subject indicated by a subject model, under the imaging conditions included in the imaging plan 6, the imaging fulfilling the examination purpose 8. The X-ray CT device 5 then generates CT image data on the basis of the reconstruction conditions included in the imaging plan 6, and generates, on the basis of the postprocessing conditions included in the imaging plan 6, the image data from the CT image data. The image data whose image quality is estimated at Step S128 are an example of first image data.

The generating function 15b then adjusts the value of tube current included in the imaging plan 50 (Step S129). For example, the generating function 15b decreases the value of tube current included in the imaging plan 50 by a predetermined value (for example, 0.1 mA) to reduce the radiation dose. At Step S129, the generating function 15b may decrease at least one of values of tube current and tube voltage included in the imaging plan 50 by a predetermined value/values (the predetermined values for the tube current and tube voltage being different from each other) to reduce the radiation dose. Furthermore, at Step S129, the generating function 15b may set the imaging plan 50 to use AEC such that the radiation dose is reduced.

On the basis of the imaging plan 50 modified at Step S129, the machine model ID 7, and the examination purpose 8, the evaluating function 15a then executes an image quality estimating simulation for estimating image quality of image data based on the imaging plan 50 (Step S130). The image data whose image quality is estimated at Step S130 are an example of second image data.

The evaluating function 15a then determines whether or not a difference between the image quality estimated at Step S128 and the image quality estimated at Step S130 is equal to or less than a predetermined threshold (Step S131). If the difference between the image quality estimated at Step S128 and the image quality estimated at Step S130 is equal to or less than the predetermined threshold, it is considered that the image quality of image data acquired on the basis of the imaging plan 50 and the image quality of image data acquired on the basis of the imaging plan 6 are approximately the same.

If the difference between the image quality estimated at Step S128 and the image quality estimated at Step S130 is larger than the predetermined threshold (Step S131: No), it is considered that the image quality of image data acquired on the basis of the imaging plan 50 and the image quality of image data acquired on the basis of the imaging plan 6 are largely different from each other. Therefore, in this case (Step S131: No), the evaluating function 15a returns to Step S129 and executes the processing from Step S129 again.

On the contrary, if the difference between the image quality estimated at Step S128 and the image quality estimated at Step S130 is equal to or less than the predetermined threshold (Step S131: Yes), the evaluating function 15a executes, on the basis of the imaging plan 50, a radiation dose estimating simulation (Step S132).

The radiation dose estimating simulation at Step S132 is a simulation for estimating a radiation dose of X-rays received by a subject indicated by a subject model in a case where the X-ray CT device 5 indicated by the machine model ID 7 performs imaging fulfilling the examination purpose 8 for the subject indicated by the subject model under the imaging conditions included in the imaging plan 50. By executing the radiation dose estimating simulation at Step S132, the evaluating function 15a estimates a radiation dose based on the imaging plan 50.

The evaluating function 15a then determines whether or not the radiation dose estimated by the radiation dose estimating simulation at Step S132 is in the range of radiation doses that has been registered in the guideline database 12a (Step S133). For example, the evaluating function 15a acquires the range of radiation doses corresponding to the examination purpose 8, from the guideline database 12a. The evaluating function 15a then determines whether or not the radiation dose estimated by the radiation dose estimating simulation is in the range of radiation doses acquired.

If the estimated radiation dose is not in the range of radiation doses (Step S133: No), it is considered that the radiation dose of X-rays received by a subject is not adequate and the imaging plan 50 needs to be improved. Therefore, in this case (Step S133: No), the evaluating function 15a returns to Step S129 and executes the processing from Step S129 again.

On the contrary, if the estimated radiation dose is in the range of radiation doses (Step S133: Yes), the radiation dose of X-rays received by a subject is considered to be adequate. In this case (Step S133: Yes), the generating function 15b proceeds to Step S134.

At Steps S128 to S133, on the basis of the evaluation result by the evaluating function 15a, the generating function 15b generates the imaging plan 50 by changing the copy (the imaging plan 50) of the imaging plan 6 so that the radiation dose estimated by the radiation dose estimating simulation falls within the range of radiation doses acquired. That is, on the basis of the evaluation result by the evaluating function 15a, the generating function 15b generates the imaging plan 50 fulfilling the guidelines, from the imaging plan 6. Therefore, the evaluation server 10 according to the first embodiment is able to obtain the imaging plan 50 not dependent on skills and experience of users. That is, the evaluation server 10 is able to obtain the imaging plan 50 that is more appropriate.

Furthermore, at Steps S128 to S133, the generating function 15b generates the imaging plan 50 such that the radiation dose estimated by the radiation dose estimating simulation falls within the recommended range of radiation doses and the difference between the image quality of image data acquired when the X-ray CT device 5 performs imaging using the imaging plan 6 and the image quality of image data acquired when the X-ray CT device 5 performs imaging using the imaging plan 50 is equal to or less than the threshold. The image data acquired when the X-ray CT device 5 performs imaging using the imaging plan 6 are an example of first image data. The image data acquired when the X-ray CT device 5 performs imaging using the imaging plan 50 are an example of second image data.

At Steps S128 to S133, the generating function 15b may execute the following processing, instead of generating the imaging plan 50 such that the difference between the image quality of image data acquired when the X-ray CT device 5 performs imaging using the imaging plan 6 and the image quality of image data acquired when the X-ray CT device 5 performs imaging using the imaging plan 50 is equal to or less than the threshold. For example, the generating function 15b may generate the imaging plan 50 such that the image quality of image data acquired when the X-ray CT device 5 performs imaging using the imaging plan 50 becomes higher than the image quality of image data acquired when the X-ray CT device 5 performs imaging using the imaging plan 6.

The generating function 15b executes, on the basis of the imaging plan 50, the machine model ID 7, and the examination purpose 8, an image data predicting simulation for predicting image data based on the imaging plan 50 (Step S134).

The image data predicting simulation at Step S134 is a simulation for predicting image data. In this simulation, the X-ray CT device 5 indicated by the machine model ID 7 performs imaging fulfilling the examination purpose 8 for a subject indicated by a subject model under the imaging conditions included in the imaging plan 50, generates, on the basis of the reconstruction conditions included in the imaging plan 50, CT image data, and generates, on the basis of the postprocessing conditions included in the imaging plan 50, the image data from the CT image data. The image data predicted at Step S134 are an example of first image data.

FIG. 9 is a diagram for explanation of an example of processing executed by the evaluation server 10 according to the first embodiment. For example, at Step S134, the generating function 15b generates image data of an image 60 illustrated in FIG. 9 by an image data predicting simulation.

The generating function 15b then executes, on the basis of the imaging plan 6, the machine model ID 7, and the examination purpose 8, an image data predicting simulation for predicting image data based on the imaging plan 6 (Step S135).

The image data predicting simulation at Step S135 is a simulation for predicting image data. In this simulation, the X-ray CT device 5 indicated by the machine model ID 7 performs imaging fulfilling the examination purpose 8 for a subject indicated by a subject model under the imaging conditions included in the imaging plan 6, generates, on the basis of the reconstruction conditions included in the imaging plan, CT image data, and generates, on the basis of the postprocessing conditions included in the imaging plan 6, the image data from the CT image data. The image data predicted at Step S135 are an example of second image data. For example, at Step S135, the generating function 15b generates image data of an image 55 illustrated in FIG. 9 by the image data predicting simulation.

At Steps S134 and S135, the generating function 15b predicts first image data acquired when the X-ray CT device 5 performs imaging using the imaging plan 6 and second image data acquired when the X-ray CT device 5 performs imaging using the imaging plan 50.

The generating function 15b then generates image data of a mark 57 illustrated in FIG. 9, the mark 57 being triangular (Step S136). The generating function 15b then stores an evaluation result group 74 (see FIG. 10), an image data group (see FIG. 10), and the imaging plans 6 and 50, into the memory 12 (Step S137).

The evaluation result group 74 includes an evaluation result 71 (see FIG. 9) generated at any one of Step S120, Step S121, Step S124, Step S126, and Step S127. The evaluation result group 74 also includes an evaluation result 72 (see FIG. 9) and an evaluation result 73 (see FIG. 9).

The following description relates to the evaluation result 72. If a result of the determination at Step S123 described above is a yes, the radiation dose based on the imaging plan 6 is in the range of radiation doses recommended by the guidelines. In this case, at Step S137, the generating function 15b generates the evaluation result 72, "Guidelines: Satisfied", that is an evaluation result indicating that the radiation dose based on the imaging plan 6 is in the range of radiation doses recommended by the guidelines. On the contrary, if a result of the determination at Step S123 described above is a no, the radiation dose based on the imaging plan 6 is not in the range of radiation doses recommended by the guidelines. In this case, at Step S137, the generating function 15b generates the evaluation result 72, "Guidelines: Unsatisfied", that is an evaluation result indicating that the radiation dose based on the imaging plan 6 is not in the range of radiation doses recommended by the guidelines.

The following description relates to the evaluation result 73. The radiation dose based on the imaging plan 50 at the time point of Step S137 is in the range of radiation doses recommended by the guidelines because the result of the determination at Step S133 described above is a yes. Therefore, at Step S137, the generating function 15b generates the evaluation result 73, "Guidelines: Satisfied", that is an evaluation result indicating that the radiation dose based on the imaging plan 50 is in the range of radiation doses recommended by the guidelines.

The image data group 70 includes image data of the image 55 generated at Step S134, image data of the image 60 generated at Step S135, and image data of the mark 57 generated at Step S136.

FIG. 10 is a diagram for explanation of an example of processing executed by the evaluation server 10 according to the first embodiment. The transmitting function 15c transmits the evaluation result group 74, the imaging plan 6, the imaging plan 50, the image data group 70, the machine model ID 7, and the examination purpose 8, to the terminal device 4 (Step S138) and ends the process. That is, the transmitting function 15c outputs the evaluation result group 74, the imaging plan 6, the imaging plan 50, the image data group 70, the machine model ID 7, and the examination purpose 8. In a specific example, the transmitting function 15c controls the communication interface 11 to transmit the evaluation result group 74, the imaging plan 6, the imaging plan 50, the image data group 70, the machine model ID 7, and the examination purpose 8, to the terminal device 4. The communication interface 11 thereby transmits the evaluation result group 74, the imaging plan 6, the imaging plan 50, the image data group 70, the machine model ID 7, and the examination purpose 8, to the terminal device 4 via the network 2.

Furthermore, the evaluating function 15a executes each of the plural steps of processing of Step S139 to Step S144 that are respectively similar to the plural steps of processing of Step S128 to Step S133. However, at Step S140, the generating function 15b increases the value of tube current included in the imaging plan 50 by a predetermined value (for example, 0.1 mA) to increase the radiation dose. At Step S140, the generating function 15b may increase at least one of values of tube current and tube voltage included in the imaging plan 50 by a predetermined value/values (the predetermined values for the tube current and tube voltage being different from each other) to increase the radiation dose. Furthermore, at Step S140, the generating function 15b may set the imaging plan 50 to use AEC such that the radiation dose is increased.

The processes illustrated in FIG. 8A, FIG. 8B, and FIG. 8C have been described above. Steps S102 to S105, S107, S108, S110 to S112, S114 to S116, S118, S119, S122, S123, S125, S128, S130 to S133, and S139 to S144 in FIG. 8A, FIG. 8B, and FIG. 8C are steps implemented by the processing circuitry 15 reading and executing the program corresponding to the evaluating function 15a, from the memory 12. Furthermore, Steps S101, S106, S109, S113, S117, S120, S121, S124, S126, S127, S129, and S134 to S137 in FIG. 8A, FIG. 8B, and FIG. 8C are steps implemented by the processing circuitry 15 reading and executing the program corresponding to the generating function 15b, from the memory 12. Furthermore, Step S138 in FIG. 8C is a step implemented by the processing circuitry 15 reading and executing the program corresponding to the transmitting function 15c, from the memory 12.

The terminal device 4 receives, as illustrated in FIG. 10, the evaluation result group 74, the imaging plan 6, the imaging plan 50, the image data group 70, the machine model ID 7, and the examination purpose 8 that have been transmitted from the evaluation server 10. The terminal device 4 displays the evaluation result group 74, the imaging plan 6, the imaging plan 50, and the image data group 70 to be checked by a user. After any necessary modification has been made to the imaging plan 50 by the user, the terminal device 4 updates the imaging plan 6 that has been registered in the imaging plan database 42a, with the imaging plan 50. Furthermore, the terminal device 4 controls the X-ray CT device 5 to update the imaging plan 6 that has been stored in the memory of the X-ray CT device 5, with the imaging plan 50.

Figure 11:
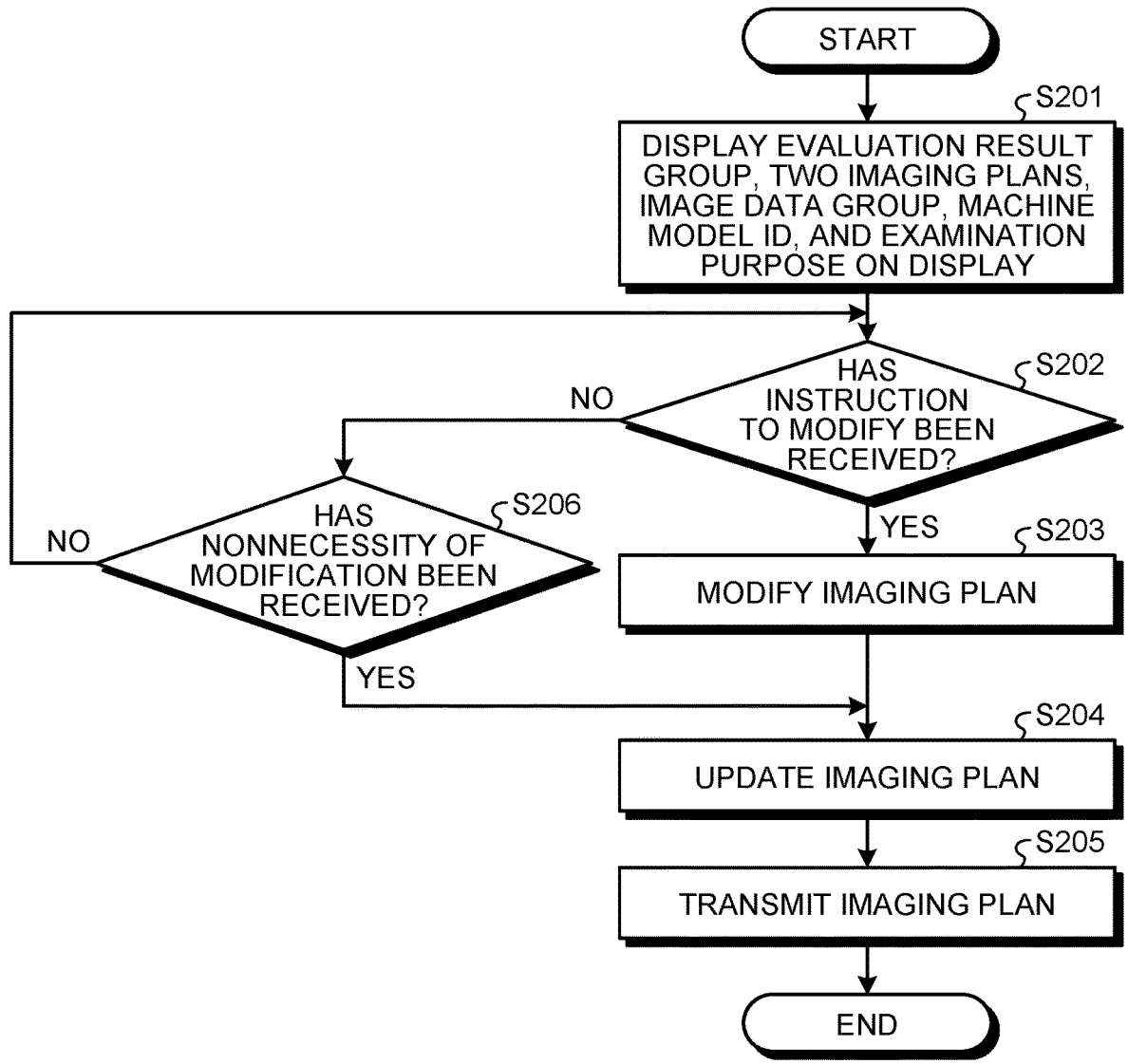
FIG. 11 is a flowchart illustrating an example of a flow of a process executed by the terminal device according to the first embodiment.

FIG. 11 is a flowchart illustrating an example of a flow of a process executed by the terminal device 4 according to the first embodiment. The process illustrated in FIG. 11 is executed when the terminal device 4 receives the evaluation result group 74, the imaging plan 6, the imaging plan 50, the image data group 70, the machine model ID 7, and the examination purpose 8 that have been transmitted from the evaluation server 10.

As illustrated in FIG. 11, the display controlling function 45d causes the evaluation result group 74, the imaging plan 6, the imaging plan 50, and the image data group 70 to be displayed on the display 44 (Step S201). For example, the display controlling function 45d causes the evaluation result group 74, the imaging plan 6, the imaging plan 50, and the image data group 70 to be displayed on the display 44 such that the evaluation result group 74, the imaging plan 6, the imaging plan 50, and the image data group 70 have positional relations that are like the positional relations illustrated in FIG. 9 described above.

For example, as illustrated in FIG. 9, the display controlling function 45d displays the imaging plan 6 and the imaging plan 50 side by side to be comparable to each other on the display 44. Therefore, the terminal device 4 enables a user to readily compare the imaging plan 6 and the imaging plan 50.

Furthermore, the display controlling function 45d displays the image 55 based on the imaging plan 6 and the image 60 based on the imaging plan 50 side by side to be comparable to each other on the display 44. Therefore, the terminal device 4 enables the user to readily compare the image 55 and the image 60.

In the case illustrated in FIG. 9, the imaging mode has been changed from "Helical" to "Conventional". Furthermore, the number of rows of X-ray detecting elements has been changed from "16" to "80". The thickness of slices collected has also been changed from "1.0" mm to "0.5" mm. Use of a tube voltage of "500" mA has been changed to use of "AEC". The rotating speed has been changed from "1.0" seconds/turn to "0.5" seconds/turn. The type of reconstruction processing has been changed from "A" to "C". The state "OFF" where no postprocessing is executed has been changed to the state where postprocessing of the type, "F", is executed.

Furthermore, as illustrated in FIG. 9, the display controlling function 45d causes the evaluation result 71 and the evaluation result 72 to be displayed in association with the imaging plan 6, on the display 44. Therefore, in the case illustrated in the example of FIG. 9, the terminal device 4 is able to let the user know that the radiation dose of X-rays to be received by a subject exceeds the recommended range of radiation doses if the X-ray CT device 5 uses the imaging plan 6. Furthermore, the terminal device 4 is able to let the user know that the imaging plan 6 needs to be improved.

As illustrated in FIG. 9, the display controlling function 45d causes the evaluation result 73 to be displayed in association with the imaging plan 50, on the display 44. Therefore, in the case illustrated in the example of FIG. 9, the terminal device 4 is able to let the user know that the radiation dose of X-rays to be received by a subject is in the recommended range of radiation doses if the X-ray CT device 5 uses the imaging plan 50.

The setting function 45e then determines whether or not an instruction to modify the imaging plan 50 has been received from the user via the input interface 43 (Step S202). The instruction to modify includes how the imaging plan 50 is to be modified.

If it has been determined that the instruction to modify the imaging plan 50 has been received (Step S202: Yes), the setting function 45e modifies the imaging plan 50 on the basis of the instruction to modify (Step S203). The setting function 45e then updates the imaging plan 6 registered in the imaging plan database 42a, with the imaging plan 50 (Step S204).

The setting function 45e then transmits the imaging plan 50 to the X-ray CT device 5 indicated by the machine model ID 7 to cause the imaging plan 6 stored in the memory of the X-ray CT device 5 to be updated with the imaging plan 50 (Step S205), and ends the process. When the processing circuitry of the X-ray CT device 5 receives the imaging plan 50, the processing circuitry updates the imaging plan 6 stored in the memory of the X-ray CT device 5, with the imaging plan 50. The imaging plan 50 is thereby stored in both the imaging plan database 42a and the memory of the X-ray CT device 5.

On the contrary, if it is determined that the instruction to modify the imaging plan 50 has not been received (Step S202: No), the setting function 45e determines whether or not information indicating that modification is unnecessary has been received from the user via the input interface 43 (Step S206). If it is determined that the information indicating that modification is unnecessary has not been received (Step S206: No), the setting function 45e returns to Step S202 and executes the processing from Step S202 again. If it is determined that the information indicating that modification is unnecessary has been received (Step S206: Yes), the setting function 45e proceeds to Step S204.

The process illustrated in FIG. 11 has been described above. Steps S201 to S205 in FIG. 11 are steps implemented by the processing circuitry 45 reading and executing the program corresponding to the setting function 45e, from the memory 42.

The first embodiment has been described above. According to this first embodiment, at Steps S106, S109, S113, S117, S129, and S140 described above, the evaluation server 10 modifies the imaging plan 50 on the basis of the performance information and the recommended range of radiation doses, for example. Therefore, the first embodiment enables acquisition of the imaging plan 50 that is more appropriate. Furthermore, according to the first embodiment, imaging plans are evaluated by the evaluation server 10, rather than by users managing the imaging plans at the respective hospitals 3. Therefore, the first embodiment enables improvement of the awareness of the users managing the imaging plans at the respective hospitals 3, the awareness being about management of radiation doses, for example. The first embodiment enables acquisition of the imaging plan 50 that enables the performance of the X-ray CT device 5 to be delivered. Therefore, improved examinations are able to be provided to subjects.

First Modified Example of First Embodiment

The case where the evaluating function 15a determines, at Step S133 and Step S144, whether or not the radiation dose estimated by the radiation dose estimating simulation is in the acquired range of radiation doses has been described above with respect to the first embodiment. However, the evaluation server 10 may bring a radiation dose estimated by a radiation dose estimating simulation closer to a specific radiation dose in an acquired range of radiation doses. Such a modified example will thus be described below as a first modified example of the first embodiment. In describing the first modified example of the first embodiment, components different from those of the first embodiment will be described mainly, and description of components that are the same as those of the first embodiment may be omitted.

For example, in this first modified example, the evaluating function 15a causes the radiation dose estimated at Step S132 or Step S143 in the case where the result of the determination at Step S133 or Step S144 is a yes, to be stored in the memory 12 for each of hospitals 3. The evaluating function 15a executes such processing every time an imaging plan 6 to be evaluated is transmitted from a terminal device 4 to the evaluation server 10. Plural radiation doses will then be stored respectively for the hospitals 3, in the memory 12. That is, the memory 12 stores the plural radiation doses respectively corresponding to the hospitals 3. The plural radiation doses stored respectively for the hospitals 3 in the memory 12 are radiation doses for the case where the result of the determination at Step S133 or Step S144 is a yes, and are thus radiation doses within the recommended range of radiation doses.

These radiation doses stored in the memory 12 are characteristic of the respective hospitals 3. For example, the radiation dose for a hospital 3 that regards image quality as important is relatively high. In contrast, the radiation dose for a hospital 3 that regards reduction of radiation doses as important is relatively low. Therefore, the evaluation server 10 according to the first modified example executes a process described below to make the estimated radiation dose closer to a radiation dose matching the characteristic of that hospital 3 and being within the recommended range of radiation doses, instead of simply causing the estimated radiation dose to be within the recommended range of radiation doses.

Figure 12:
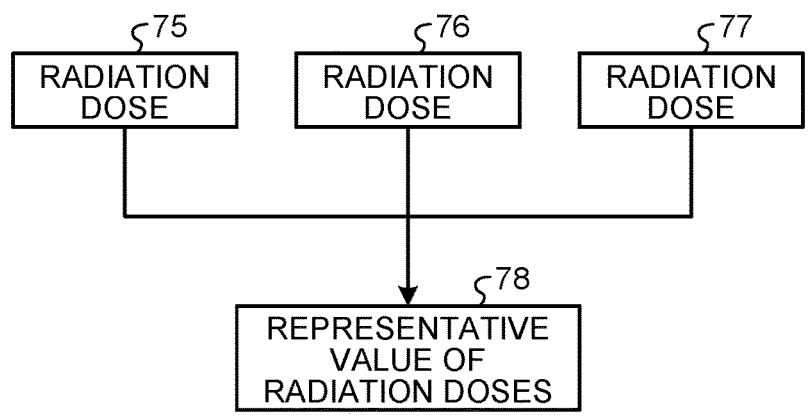
FIG. 12 is a diagram for explanation of an example of processing executed by an evaluation server according to a first modified example of the first embodiment.

For example, at Step S133 and Step S144, the evaluating function 15a acquires, from the memory 12, plural radiation doses corresponding to the hospital 3 that has transmitted the imaging plan 6. FIG. 12 is a diagram for explanation of an example of processing executed by the evaluation server 10 according to the first modified example of the first embodiment. For example, the evaluating function 15a acquires, from the memory 12, plural radiation doses 75 to 77 corresponding to the hospital 3 that has transmitted the imaging plan 6.

At Step S133 and Step S144, the evaluating function 15a then calculates a representative value 78 of the plural radiation doses 75 to 77. For example, the evaluating function 15a calculates, as the representative value 78, the mean or median of the plural radiation doses 75 to 77. The representative value 78 is an example of a specific value. Furthermore, because the radiation doses 75 to 77 are within the recommended range of radiation doses, the representative value 78 is also within the recommended range of radiation doses.

At Step S133 and Step S144, the evaluating function 15a determines whether or not a difference between the representative value 78 and the radiation dose estimated by the radiation dose estimating simulation at Step S132 or Step S143 is equal to or less than a predetermined threshold. If it is determined that the difference between the representative value 78 and the estimated radiation dose is equal to or less than the predetermined threshold, the evaluating function 15a proceeds to Step S134. On the contrary, if it is determined that the difference between the representative value 78 and the estimated radiation dose is larger than the predetermined threshold, the evaluating function 15a returns to Step S129 or Step S140.

As described above, in this first modified example, the estimated radiation dose in the case where the results of the determination at Step S133 and Step S144 are each a yes is able to be made closer to the representative value 78. Specifically, the difference between the estimated radiation dose and the representative value 78 becomes equal to or less than the predetermined value. Therefore, at Step S129 and Step S140, the generating function 15b generates the imaging plan 50 such that the difference between the estimated radiation dose and the representative value 78 in the recommended range of radiation doses becomes equal to or less than the threshold. Accordingly, the evaluation server 10 according to this first modified example enables generation of the imaging plan 50 matching the characteristics of each hospital 3.

In this first modified example, the evaluating function 15a may calculate a representative value from plural radiation doses corresponding to a specific hospital 3 and use the calculated representative value instead of the representative value 78. This specific hospital 3 is, for example, a hospital famous for their high image quality.

Second Modified Example of First Embodiment

At Step S138, the transmitting function 15c may transmit a program of reconstruction processing of the type included in the imaging plan 50 to the terminal device 4 when the type of reconstruction processing included in the imaging plan 6 is different from the type of reconstruction processing included in the imaging plan 50. Furthermore, at Step S138, the transmitting function 15c may transmit a program of postprocessing of the type included in the imaging plan 50 if the type of postprocessing included in the imaging plan 6 is different from the type of postprocessing included in the imaging plan 50. Such a modified example will thus be described below as a second modified example of the first embodiment. In describing the second modified example of the first embodiment, components different from those of the first embodiment will be described mainly, and description of components that are the same as those of the first embodiment may be omitted.

For example, in the second modified example, programs of reconstruction processing of all of types that are able to be used by the X-ray CT device 5 have been stored in the memory 12. Furthermore, programs of postprocessing of all of types that are able to be used by the X-ray CT device 5 have also been stored in the memory 12.

At Step S138, the transmitting function 15c acquires a program of reconstruction processing of the type included in the imaging plan 50 from the memory 12 if the type of reconstruction processing included in the imaging plan 6 is different from the type of reconstruction processing included in the imaging plan 50. At Step S138, the transmitting function 15c then transmits the program acquired, to the terminal device 4.

Furthermore, at Step S138, the transmitting function 15c acquires, from the memory 12, a program of postprocessing of the type included in the imaging plan 50, if the type of postprocessing included in the imaging plan 6 is different from the type of postprocessing included in the imaging plan 50. At Step S138, the transmitting function 15c then transmits the program acquired, to the terminal device 4.

When the terminal device 4 receives the program transmitted from the evaluation server 10, the terminal device 4 transmits the program to the X-ray CT device 5. When the X-ray CT device 5 receives the program transmitted from the terminal device 4, the X-ray CT device 5 performs installation of the program.

For example, the X-ray CT device 5 may not have, installed thereon, the program of the reconstruction processing included in the imaging plan 50 and the program of the postprocessing included in the imaging plan 50. In that case, the X-ray CT device 5 performs installation of these programs. Therefore, the evaluation server 10 according to the second modified example is able to cause the X-ray CT device 5 to perform installation of the programs without making the user provide the programs.

When such processing is executed upon installation of the X-ray CT device 5, the X-ray CT device 5 is able to use many programs when the X-ray CT device 5 has been installed. As a result, the X-ray CT device 5 is able to use many imaging plans that have been preset. The imaging plans may also be called protocols.

In a case where a certain time period (for example, one year) has elapsed since the installation of the X-ray CT device 5, the X-ray CT device 5 or the terminal device 4 preferably holds necessary programs and imaging plans in a usable state by classifying programs and imaging plans that are able to be used by the X-ray CT device 5 into the necessary ones and unnecessary ones.

Furthermore, when performing imaging, the X-ray CT device 5 displays plural imaging plans that have been preset, the plural imaging plans corresponding to a region specified by a user. The X-ray CT device 5 then lets the user specify an imaging plan to be used in the imaging, from the plural imaging plans.

When displaying the plural imaging plans that have been preset, the X-ray CT device 5 may sort the plural imaging plans according to their frequencies of use. For example, the X-ray CT device 5 may display the plural imaging plans from the top in descending order of frequency of use.

Furthermore, the X-ray CT device 5 may display an imaging plan known to be used on a particular cycle (for example, every Friday) such that the imaging plan is positioned higher in the sequence on those days (for example, on Fridays).

A cloud server may perform the reconstruction processing and postprocessing and the X-ray CT device 5 may receive results of the processing by the cloud server. In this case, the memory 12 does not store the programs. At Step S138, the transmitting function 15c transmits the use procedure for causing the cloud server to execute reconstruction processing of the type included in the imaging plan 50, to the terminal device 4, when the type of reconstruction processing included in the imaging plan 6 is different from the type of reconstruction processing included in the imaging plan 50. Furthermore, at Step S138, the transmitting function 15c transmits the use procedure for causing the cloud server to execute postprocessing of the type included in the imaging plan 50, to the terminal device 4, when the type of postprocessing included in the imaging plan 6 is different from the type of postprocessing included in the imaging plan 50. In this case, the evaluation server 10 according to the second modified example enables a user to know the use procedures for the cloud server without making the user find the use procedures.

In addition, a reconstructing server that performs reconstruction and a postprocessing server that performs postprocessing may be provided separately from the X-ray CT device 5, in the same intranet.

According to the above description of the embodiments, the processing circuitry 15 executes the plural functions, but the embodiments are not limited to this description. For example, plural pieces of processing circuitry may be provided and the plural pieces of processing circuitry may execute their functions respectively.

Third Modified Example of First Embodiment

In the first embodiment, the content registered in the guideline database 12a and performance information database 12b is updated with the most recent content. The evaluation server 10 then may perform control to let a user know that the content registered in the guideline database 12a or the performance information database 12b has been updated with the most recent content. Such a modified example will thus be described below as a third modified example of the first embodiment. In describing the third modified example of the first embodiment, components different from those of the first embodiment will be described mainly, and description of components that are the same as those of the first embodiment may be omitted.

FIG. 13A is a diagram illustrating an example of a data structure of a guideline database 12a according to the third modified example of the first embodiment. FIG. 13B is a diagram illustrating an example of a data structure of a performance information database 12b according to the third modified example of the first embodiment.

An evaluation server 10 according to the third modified example is different from the evaluation server 10 according to the first embodiment in that the evaluation server 10 according to the third modified example performs various types of processing using the guideline database 12a illustrated in FIG. 13A and the performance information database 12b illustrated in FIG. 13B, instead of the guideline database 12a illustrated in FIG. 6 and the performance information database 12b illustrated in FIG. 7.

As illustrated in FIG. 13A, in the third modified example, the guideline database 12a has, registered therein, plural records each having an item, "Examination Purpose", an item, "Range of Radiation Doses", an item, "Any Update", and an item, "Date of Update". That is, each record registered in the guideline database 12a has an item, "Examination Purpose", an item, "Range of Radiation Doses", an item, "Any Update", and an item, "Date of Update", in association with one another. The guideline database 12a has, registered therein, a plurality of these records.

Similarly to the first embodiment, for the item, "Examination Purpose", the examination purpose is registered, and for the item, "Range of Radiation Doses", the range of radiation doses corresponding to the examination purpose and recommended in various guidelines is registered.

For the item, "Any Update", information indicating whether or not the range of radiation doses registered for the item, "Range of Radiation Doses", has been updated is registered. For example, if the range of radiation doses registered for the item, "Range of Radiation Doses", has been updated, the processing circuitry 15 registers a value, "1", indicating that the range of radiation doses has been updated, for the item, "Any Update". On the contrary, if the range of radiation doses registered for the item, "Range of Radiation Doses", has not been updated, the processing circuitry 15 registers a value, "0", indicating that the range of radiation doses has not been updated, for the item, "Any Update".

For the item, "Date of Update", the date on which the range of radiation doses registered for the item, "Range of Radiation Doses" was updated is registered. For example, if the range of radiation doses registered for the item, "Range of Radiation Doses", has been updated, the processing circuitry 15 registers the date on which the range of radiation doses was updated, for the item, "Date of Update". If the range of radiation doses has not been updated, a null value is registered for the item, "Date of Update".

As illustrated in FIG. 13B, in the third modified example, the performance information database 12b has, registered therein, plural records each having an item, "Machine Model ID", an item, "Performance Information", an item, "Any Update", and an item, "Date of Update". That is, each record registered in the performance information database 12b has an item, "Machine Model ID", an item, "Performance Information", an item, "Any Update", and an item, "Date of Update", in association with one another. The performance information database 12b has, registered therein, a plurality of these records.

Similarly to the first embodiment, for the item, "Machine Model ID", the machine model ID is registered, and for the item, "Performance Information", the performance information is registered.

For the item, "Any Update", information indicating whether or not the performance registered for the item, "Performance Information", has been updated is registered. For example, if the performance information registered for the item, "Performance Information", has been updated, the processing circuitry 15 registers the value, "1", indicating that the performance information has been updated, for the item, "Any Update". On the contrary, if the performance information registered for the item, "Performance Information", has not been updated, the processing circuitry 15 registers the value, "0", indicating that the performance information has not been updated, for the item, "Any Update".

For the item, "Date of Update", the date on which the performance information registered for the item, "Performance Information", was updated is registered. For example, if the performance information registered for the item, "Performance Information", has been updated, the processing circuitry 15 registers the date on which the performance information was updated, for the item, "Date of Update". If the performance information has not been updated, a null value is registered for the item, "Date of Update".

At Step S136 (see FIG. 8C) in the third modified example, the generating function 15b executes processing similar to the processing in the first embodiment and the evaluating function 15a executes the following processing. For example, the evaluating function 15a identifies a record having the examination purpose 8 registered for the item, "Examination Purpose", from all of the records in the guideline database 12a, the examination purpose 8 having been transmitted from the terminal device 4. The evaluating function 15a then acquires a value registered for the item, "Any Update", in the record identified.

If the value acquired is "1", the range of radiation doses has been updated. In the case where the acquired value is "1", the evaluating function 15a acquires the date registered for "Date of Update" in the identified record. The date acquired herein is the date on which the range of radiation doses was updated.

Furthermore, at Step S136, the evaluating function 15a further executes the following processing. For example, the evaluating function 15a identifies a record having the machine model ID 7 registered for the item, "Machine Model ID", from all of the records in the performance information database 12b, the machine model ID 7 having been transmitted from the terminal device 4. The evaluating function 15a then acquires a value registered for the item, "Any Update", in the record identified.

If the value acquired is "1", the performance information has been updated. In the case where the acquired value is "1", the evaluating function 15a then acquires the date registered for "Date of Update" in the identified record. The date acquired herein is the date on which the performance information was updated.

At Step S137, the generating function 15b performs processing similar to that in the first embodiment and further executes the following processing. For example, if the date on which the range of radiation doses was updated is acquired at Step S136, the generating function 15b stores the date on which that range of radiation doses was updated, into the memory 12. Furthermore, if the date on which the performance information was updated is acquired at Step S136, the generating function 15b stores the date on which the performance information was updated, into the memory 12.

At Step S138, the transmitting function 15c performs processing similar to that in the first embodiment and further performs the following processing. For example, if the date on which the range of radiation doses was updated is acquired at Step S136, the transmitting function 15c transmits the date on which the range of radiation doses was updated, to the terminal device 4. If the date on which the performance information was updated is acquired at Step S136, the transmitting function 15c transmits the date on which the performance information was updated, to the terminal device 4.

That is, if at least one of the range of radiation doses and performance information has been updated, the transmitting function 15c outputs information indicating that the at least one of them has been updated.

In the third modified example, similarly to the first embodiment, the terminal device 4 receives the evaluation result group 74, the imaging plan 6, the imaging plan 50, the image data group 70, the machine model ID 7, and the examination purpose 8 that have been transmitted from the evaluation server 10. Furthermore, if the date on which the range of radiation doses was updated is acquired at Step S136, the terminal device 4 receives the date on which the radiation doses was updated. In addition, if the date on which the performance information was updated is acquired at Step S136, the terminal device 4 receives the date on which the performance information was updated.

Similarly to the first embodiment, the terminal device 4 then displays the evaluation result group 74, the imaging plan 6, the imaging plan 50, and the image data group 70 to let a user check them. In addition, if the date on which the range of radiation doses was updated is received, the terminal device 4 displays the received date on which the range of radiation doses was updated. Furthermore, if the date on which the performance information was updated is received, the terminal device 4 displays the received date on which the performance information was updated.

FIG. 14 is a diagram illustrating an example of display according to the third modified example of the first embodiment. The example illustrated in FIG. 14 corresponds to a case where the terminal device 4 has not received a date on which the range of radiation doses was updated, but has received a date, "Y1/M1/D1", on which the performance information was updated. As illustrated in FIG. 14, similarly to the first embodiment, the terminal device 4 displays an evaluation result group 74, an imaging plan 6, an imaging plan 50, and an image data group 70. Furthermore, as illustrated in FIG. 14, the terminal device 4 displays a message, "Performance information updated: Y1/M1/D1", indicating the date on which the performance information was updated. The user is thereby able to know that the performance information was updated on Y1/M1/D1.

Fourth Modified Example of First Embodiment

The case where the evaluation server 10 outputs an evaluation result based on a range of radiation doses and performance information of a time after an update of at least one of a range of radiation doses and performance information has been described with respect to the third modified example. However, the evaluation server 10 may output, in addition to an evaluation result based on a range of radiation doses and performance information of a time after an update of at least one of a range of radiation doses and performance information, an evaluation result based on the range of radiation doses and performance information of a time before the update of the at least one of the range of radiation doses and the performance information. Such a modified example will thus be described below as a fourth modified example of the first embodiment. In describing the fourth modified example, components different from those of the third modified example will be described mainly, and description of components that are the same as those of the third modified example may be omitted.

FIG. 15A is a diagram illustrating an example of a data structure of a guideline database 12a according to the fourth modified example of the first embodiment. FIG. 15B is a diagram illustrating an example of a data structure of a performance information database 12b according to the fourth modified example of the first embodiment.

An evaluation server 10 according to the fourth modified example is different from the evaluation server 10 according to the third modified example in that the evaluation server 10 according to the fourth modified example performs various types of processing using the guideline database 12a illustrated in FIG. 15A and the performance information database 12b illustrated in FIG. 15B, instead of the guideline database 12a illustrated in FIG. 13A and the performance information database 12b illustrated in FIG. 13B.

As illustrated in FIG. 15A, in the fourth modified example, the guideline database 12a has, registered therein, plural records each having an item, "Examination Purpose", an item, "Range of Radiation Doses", an item, "Any Update", an item, "Date of Update", and an item, "Range of Radiation Doses Before Update". That is, each record registered in the guideline database 12a has an item, "Examination Purpose", an item, "Range of Radiation Doses", an item, "Any Update", an item, "Date of Update", and an item, "Range of Radiation Doses Before Update", in association with one another. The guideline database 12a has, registered therein, a plurality of these records.

Among these items, for the item, "Examination Purpose", the item, "Range of Radiation Doses", the item, "Any Update", and the item, "Date of Update", content similar to that in the third modified example is registered.

For the item, "Range of Radiation Doses Before Update", a range of radiation doses before an update is registered. For example, if an update of a range of radiation doses that has been registered for the item, "Range of Radiation Doses", has been made, the evaluating function 15a of the processing circuitry 15 registers the range of radiation doses of a time before the update, for the item, "Range of Radiation Doses Before Update". If the range of radiation doses has not been updated, a null value is registered for the item, "Range of Radiation Doses Before Update".

As illustrated in FIG. 15B, in the fourth modified example, the performance information database 12b has, registered therein, plural records each having an item, "Machine Model ID", an item, "Performance Information", an item, "Any Update", an item, "Date of Update", an item, "Performance Information Before Update", and an item, "Content of Update". That is, each record registered the performance information database 12b has an item, "Machine Model ID", an item, "Performance Information", an item, "Any Update", an item, "Date of Update", an item, "Performance Information Before Update", and an item, "Content of Update", in association with one another. The performance information database 12b has, registered therein, a plurality of these records.

Among these items, for the item, "Machine Model ID", the item, "Performance Information", the item, "Any Update", and the item, "Date of Update", content similar to that in the third modified example is registered.

For the item, "Performance Information Before Update", performance information before the update is registered. For example, if an update of performance information registered for the item, "Performance Information", has been made, the evaluating function 15a registers the performance information of a time before the update, for the item, "Performance Information Before Update". If the performance information has not been updated, a null value is registered for the item, "Performance Information Before Update".

Content of the update is registered for the item, "Content of Update". If an update of performance information registered for the item, "Performance Information", has been made, the evaluating function 15a registers content of the update for the item, "Content of Update". The content of the update is information indicating how the performance information was updated. For example, the content of the update is information indicating which of imaging conditions, reconstruction conditions, and postprocessing conditions that are included in the performance information has/have been updated in what way/ways. Specifically, for example, if the type of postprocessing, "F", has been updated with the type of postprocessing, "G", the evaluating function 15a registers content of the update indicating that the type of postprocessing, "F", has been updated with the type of postprocessing, "G", for the item, "Content of Update".

If the performance information has not been updated, a null value is registered for the item, "Content of Update".

The generating function 15b then performs processing similar to the processing in the third modified example at Step S136 (see FIG. 8C).

In the fourth modified example, the evaluation server 10 executes the following processing at a step that is between Step S136 and Step S137. This step that is between Step S136 and Step S137 will hereinafter be referred to as "Step S301".

At Step S301, for example, if the value acquired at Step S136 (the value registered for the item, "Any Update", in the guideline database 12a) is "1", the evaluating function 15a acquires the range of radiation doses of a time before the update, the range of radiation doses having been registered for the item, "Range of Radiation Doses Before Update".

Furthermore, at Step S301, if the value acquired at Step S136 (the value registered for the item, "Any Update", in the performance information database 12b) is "1", the evaluating function 15a acquires the performance information of a time before the update, the performance information having been registered for the item, "Performance Information Before Update". In addition, if the value acquired at Step S136 (the value registered for the item, "Any Update", in the performance information database 12b) is "1", the evaluating function 15a acquires the content of the update that has been registered for the item, "Content of Update".

The following four cases may be considered for Step S301. The first case is a case where a range of radiation doses before the update and performance information before the update are acquired because both the range of radiation doses and the performance information have been updated. The second case is a case where a range of radiation doses before the update is acquired because the range of radiation doses from the range of radiation doses and the performance information has been updated. The third case is a case where performance information before the update is acquired because the performance information from the range of radiation doses and the performance information has been updated. The fourth case is a case where both the range of radiation doses and the performance information have not been updated.

In the fourth case, the evaluation server 10 proceeds to Step S137, and similarly to the third modified example, executes the processing from Step S137.

On the contrary, in the first case, at Step S301, the evaluation server 10 executes processing similar to the processing at Steps S101 to S135 and S139 to S144, by using the range of radiation doses of the time before the update and the performance information of the time before the update. That is, the evaluation server 10 executes processing using the range of radiation doses of the time before the update and the performance information of the time before the update, instead of the performance information acquired at Step S102 and the range of radiation doses corresponding to the examination purpose 8. The evaluation server 10 then proceeds to Step S137.

At Step S137, similarly to the third modified example, the generating function 15b stores various types of information acquired by the processing at Steps S101 to S135 and S139 to S144, into the memory 12, and further executes the following processing. For example, similarly, the generating function 15b stores the various types of information acquired by the processing at Step S301, into the memory 12. The various types of information acquired by the processing at Step S301 include an imaging plan 50a (see FIG. 16), an evaluation result 73a (see FIG. 16), image data on an image 60a (see FIG. 16), and content of update.

At Step S138, the transmitting function 15c transmits, similarly to the third modified example, the various types of information acquired by the processing at Steps S101 to S135 and S139 to S144, to the terminal device 4, and further executes the following processing. For example, the transmitting function 15c similarly transmits the various types of information acquired by the processing at Step S301, to the terminal device 4.

In the fourth modified example, the terminal device 4 receives the various types of information transmitted from the evaluation server 10. FIG. 16 is a diagram illustrating an example of display according to the fourth modified example of the first embodiment.

As illustrated in FIG. 16, the display controlling function 45d of the terminal device 4 displays the imaging plan 50, the evaluation result 73, and the image 60, on the display 44, in association with text data, "After Update". In the fourth modified example, the display controlling function 45*d* further displays the imaging plan 50*a*, the evaluation result 73*a*, and the image 60*a*, on the display 44, in association with text data, "Before Update".

If the content of update indicates that the type of postprocessing, "F", has been updated with the type of postprocessing, "G", the display controlling function 45*d* highlights the type of postprocessing, "F", and the type of postprocessing, "G", as illustrated in FIG. 16. A user is thereby able to readily know that the type of postprocessing, "F", has been updated with the type of postprocessing, "G".

After at least one of a range of radiation doses and performance information has been updated, an imaging plan, an evaluation result, and an image (hereinafter, referred to as the "imaging plan etc.") that are based on the range of radiation doses and performance information after the update of the at least one of them and an imaging plan etc. based on the range of radiation doses and performance information before the update of the at least one of them may be not constantly displayed at the terminal device 4. For example, the imaging plan etc. based on the range of radiation doses and performance information after the update of the at least one of them and the imaging plan etc. based on the range of radiation doses and performance information before the update of the at least one of them may be displayed at the terminal device 4 during a predetermined time period after the update of the at least one of the range of radiation doses and performance information. After elapse of the predetermined time period, the imaging plan etc. based on the range of radiation doses and performance information after the update of the at least one of them may be displayed at the terminal device 4.

In this case, for example, at Step S138, the transmitting function 15*c* of the evaluation server 10 may transmit the various types of information acquired by the processing of Steps S101 to S135 and S139 to S144 and the various types of information acquired by the processing of Step S301, to the terminal device 4, over a predetermined time period from the date on which the range of radiation doses was updated acquired at Step S136 or the date on which the performance information was updated. Furthermore, at Step S138, the transmitting function 15*c* may transmit the various types of information acquired by the processing of Steps S101 to S135 and S139 to S144, to the terminal device 4 after elapse of the predetermined time period.

In both the second case and the third case, the evaluation server 10 executes processing similar to the processing in the fourth case.

However, in the second case, at Step S301, the evaluation server 10 executes processing similar to the processing of Steps S101 to S135 and S139 to S144, by using the range of radiation doses of a time before the update. That is, the evaluation server 10 executes processing using the range of radiation doses of a time before the update, instead of the range of radiation doses corresponding to the examination purpose 8.

Furthermore, in the third case, at Step S301, the evaluation server 10 executes processing similar to the processing of Steps S101 to S135 and S139 to S144, by using the performance information of a time before the update. That is, the evaluation server 10 executes processing using the performance information of a time before the update, instead of the performance information acquired at Step S102.

As described above, if at least one of performance information and a range of radiation doses has been updated, the evaluation server 10 according to the fourth modified example outputs the imaging plan 50*a*, evaluation result 73*a*, and data on the image 60*a* that are based on the performance information and range of radiation doses of a time before the update of the at least one of them, and the imaging plan 50, evaluation result 73, and data on the image 60*a* that are based on the performance information and range of radiation doses of a time after the update of the at least one of them.

Furthermore, if at least one of the performance information and the range of radiation doses has been updated, the evaluation server 10 outputs, for a predetermined time period after the update of the at least one of the performance information and the range of radiation doses, the imaging plan 50*a*, evaluation result 73*a*, and data on the image 60*a* that are based on the performance information and range of radiation doses of a time before the update of the at least one of them and the imaging plan 50, evaluation result 73, and data on the image 60*a* that are based on the performance information and range of radiation doses of a time after the update of the at least one of them.

Furthermore, if at least one of the performance information and the range of radiation doses has been updated, the evaluation server 10 outputs the above described content of update as information enabling comparison between: the performance information and range of radiation doses of a time before the update of the at least one of them; and the performance information and range of radiation doses of a time after the update of the at least one of them. For example, in the fourth modified example, by the evaluation server 10 outputting content of update indicating that the type of postprocessing, "F", has been updated with the type of postprocessing, "G", to the terminal device 4, the type of postprocessing, "F", and the type of postprocessing, "G" are highlighted to enable comparison when being displayed at the terminal device 4. Therefore, the content of update indicating that the type of postprocessing, "F", has been updated with the type of postprocessing, "G", is information enabling comparison between the performance information of a time before the update and the performance information of a time after the update.

Fifth Modified Example of First Embodiment

The case where the evaluation server 10 outputs content of update as information enabling comparison between performance information before the update and performance information after the update, to the terminal device 4 has been described above with respect to the fourth modified example. In this case, conditions before the update and conditions after the update are displayed at the terminal device 4 to be comparable to each other regardless of whether or not they are the conditions (imaging conditions, reconstruction conditions, or postprocessing conditions) that a user wants to know.

Therefore, conditions displayed to be comparable to each other may sometimes be not the conditions that a user wants to know. The evaluation server 10 may thus output a condition for which a user wants to know whether the condition has been updated, to the terminal device 4, and the terminal device 4 may display the conditions before and after the update to be comparable to each other, the conditions being those that the user want to know. Such a modified example will thus be described below as a fifth modified example of the first embodiment. In describing the fifth modified example, components different from those of the fourth modified example will be described mainly, and description of components that are the same as those of the fourth modified example may be omitted.

In the fifth modified example, the evaluation requesting function 45c of the terminal device 4 transmits a search key, in addition to the imaging plan 6 to be evaluated, the machine model ID 7, and the examination purpose 8 that are illustrated in FIG. 4, to cause the evaluation server 10 to evaluate the imaging plan 6.

The search key is information indicating a condition specified by a user, from an imaging condition, a reconstruction condition, and a postprocessing condition. It is assumed herein that the user wants to know if a certain condition has been updated. Such a condition differs depending on users. The user thus inputs a search key that is information indicating the condition that the user wants to know about, via the input interface 43, to the processing circuitry 45. That is, information indicating the condition specified by the user is input as the search key via the input interface 43 to the processing circuitry 45. For example, if the user want to know of any update of a type of postprocessing, information indicating the type of postprocessing is input as the search key.

In the fifth modified example, at Step S138, the transmitting function 15c transmits the various types of information acquired by the processing of Steps S101 to S135 and S139 to S144, to the terminal device 4, similarly to the fourth modified example. Furthermore, at Step S138, similarly to the fourth modified example, the transmitting function 15c transmits the various types of information acquired by the processing of Step S301, to the terminal device 4.

In addition, in this fifth modified example, at Step S138, the transmitting function 15c determines whether or not two conditions match each other, the two conditions being a condition that is indicated by the content of update and has been updated and the condition indicated by the search key. For example, if the content of update indicates that a type of postprocessing has been updated and the search key indicates the type of postprocessing, the transmitting function 15c determines that the two conditions match each other. If it is determined that the two conditions match each other, at Step S138, the transmitting function 15c transmits an instruction to the terminal device 4, the instruction causing display of how the type of postprocessing indicated by the content of update has been updated. For example, the transmitting function 15c transmits an instruction to the terminal device 4, the instruction causing display of the fact that the type of processing, "F", has been updated with the type of postprocessing, "G".

That is, in a case where performance information has been updated, when the updated condition included in the performance information and the specified condition match each other, the transmitting function 15c outputs the updated condition.

As a result, the terminal device 4 displays the imaging plans 50 and 50a, the evaluation results 73 and 73a, the images 60 and 60a, etc. on the display 44, and on the basis of the instruction described above, displays also a message, "Type of processing F has been updated with type of postprocessing G.", on the display 44, the message indicating that the type of postprocessing, "F", has been updated with the type of postprocessing, "G". The user is thereby able to readily know how the condition specified by the user has been updated.

Because how the condition specified by the user has been updated is displayed on the display 44, the terminal device 4 may be configured to not display the imaging plan 50a, the evaluation result 73a, the image 60a, etc. on the display 44.

In this case, at Step S138, the transmitting function 15c may be configured to not transmit the various types of information acquired by the processing of Step S301, the various types of information being other than the content of update, to the terminal device 4.

Sixth Modified Example of First Embodiment

A case where an imaging plan 6 is evaluated using a certain recommended range of radiation doses (hereinafter, "a first range of radiation doses") and certain performance information (hereinafter, "first performance information") in the fourth modified example will now be considered. In this case, at the time when at least one of the first range of radiation doses and the first performance information is updated, the evaluation server 10 may evaluate the imaging plan 6 by using a recommended range of radiation doses (hereinafter, "second range of radiation doses") and performance information (hereinafter, "second performance information") of a time after the update of the at least one of the first range of radiation doses and the first performance information.

The evaluation server 10 may then output an imaging plan 50a, an evaluation result 73a, and an image 60a that are based on the first range of radiation doses and first performance information, and an imaging plan 50, an evaluation result 73, and an image 60 that are based on the second range of radiation doses and second performance information.

Such a modified example will thus be described below as a sixth modified example of the first embodiment. In describing the sixth modified example, components different from those of the fourth modified example will be described mainly, and description of components that are the same as those of the fourth modified example may be omitted.

In the sixth modified example, the evaluating function 15a stores the imaging plan 50a, the evaluation result 73a, and image data on the image 60a that are based on the first range of radiation doses and first performance information, into the memory 12.

At the time when at least one of the first range of radiation doses and first performance information is updated, the evaluating function 15a then acquires the imaging plan 50, evaluation result 73, and data on the image 60 that are based on the second range of radiation doses and second performance information.

Similarly to the fourth modified example, the transmitting function 15c transmits the imaging plan 50a, evaluation result 73a, and data on the image 60a, and the imaging plan 50, evaluation result 73, and data on the image 60, to the terminal device 4. Therefore, a user is able to readily compare the imaging plan 50a, evaluation result 73a, and image 60a that are based on the recommended range of radiation doses and performance information of a time before the update of the at least one of them, to the imaging plan 50, evaluation result 73, and image 60 that are based on the recommended range of radiation doses and performance information of a time after the update of the at least one of them.

As described above, in a case where at least one of a recommended range of radiation doses and performance information has been updated, the transmitting function 15c outputs an imaging plan 50a, an evaluation result 73a, and image data on an image 60a that are based on the recommended range of radiation doses and performance information of a time before the update of the at least one of them and an imaging plan 50, an evaluation result 73, and data on an image 60 that are based on a recommended range of radiation doses and performance information of a time after the update of the at least one of them.

Seventh Modified Example of First Embodiment

As described above, users manage imaging plans according to functions of X-ray CT devices 5 and circumstances at facilities, such as hospitals 3. For example, a specialist who manages imaging plans may adjust imaging conditions, reconstruction conditions, postprocessing conditions, etc. included in the imaging plans, according to functions of an X-ray CT device 5 and circumstances at a facility, such as a hospital 3. The specialist may thus adjust the imaging conditions, reconstruction conditions, postprocessing conditions, etc. manually. Such a specialist may also be called an application specialist.

If a specialist has adjusted an imaging plan manually as described above, the imaging plan that has been adjusted is considered to be an imaging plan suitable for functions of the X-ray CT device 5 and circumstance at the facility, such as the hospital 3. The evaluation server 10 may thus be configured to not evaluate any imaging plan that has been adjusted manually. Such a modified example will thus be described below as a seventh modified example of the first embodiment. In describing the seventh modified example, components different from those of the first embodiment will be described mainly, and description of components that are the same as those of the first embodiment may be omitted.

FIG. 17 is a diagram illustrating an example of a data structure of an imaging plan database 42*a* according to the seventh modified example of the first embodiment.

An evaluation server 10 according to the seventh modified example is different from the evaluation server 10 according to the first embodiment in that the evaluation server 10 according to the seventh modified example performs various types of processing using the imaging plan database 42*a* illustrated in FIG. 17, instead of the imaging plan database 42*a* illustrated in FIG. 3.

As illustrated in FIG. 17, in the seventh modified example, the imaging plan database 42*a* has, registered therein, plural records each having an item, "Machine Model ID", an item, "Examination Purpose", an item, "Imaging Plan", an item, "Any Manual Adjustment", and an item, "Date of Manual Adjustment". That is, each record registered in the imaging plan database 42*a* has an item, "Machine Model ID", an item, "Examination Purpose", an item, "Imaging Plan", an item, "Any Manual Adjustment", and an item, "Date of Manual Adjustment", in association with one another. The imaging plan database 42*a* has, registered therein, a plurality of these records.

Among these items, for the item, "Machine Model ID", the item, "Examination Purpose", and the item, "Imaging Plan", content similar to that in the first embodiment is registered.

For the item, "Any Manual Adjustment", information indicating whether or not the imaging plan registered for the item, "Imaging Plan", has been adjusted manually is registered. For example, a specialist manually adjusts an imaging plan to be adjusted from plural imaging plans that have been preset. Specifically, a specialist inputs, via the input interface 13, an instruction for adjusting an imaging plan, to the processing circuitry 15. On the basis of the instruction input, the processing circuitry 15 adjusts the imaging plan registered for the item, "Imaging Plan". When that is done, the processing circuitry 15 registers a value, "1", indicating that the imaging plan has been adjusted manually, for the item, "Any Manual Adjustment". In contrast, if the processing circuitry 15 has not adjusted the imaging plan, the processing circuitry 15 registers a value, "0", indicating that the imaging plan has not been adjusted manually, for the item, "Any Manual Adjustment".

For the item, "Date of Manual Adjustment", the date on which the imaging plan registered for the item, "Imaging Plan", was adjusted is registered. For example, if the imaging plan registered for the item, "Imaging Plan", has been adjusted, the processing circuitry 15 registers the date on which the imaging plan was adjusted, for the item, "Date of Manual Adjustment". If the imaging plan has not been adjusted, a null value is registered for the item, "Date of Manual Adjustment".

In the seventh modified example. the evaluation requesting function 45*c* of the terminal device 4 transmits, in addition to the imaging plan 6 to be evaluated, the machine model ID 7, and the examination purpose 8 that are illustrated in FIG. 4, the value registered (0 or 1) for the item, "Any Manual Adjustment", to the evaluation server 10 to cause the evaluation server 10 to evaluate the imaging plan 6. Furthermore, if the value registered for the item, "Any Manual Adjustment", is "1", the evaluation requesting function 45*c* transmits the date on which the imaging plan was adjusted, to the evaluation server 10, the date having been registered for the item, "Date of Manual Adjustment".

If the value registered for the item, "Any Manual Adjustment", is "0", that is, if the imaging plan 6 has not been adjusted manually, the evaluating function 15*a* of the evaluation server 10 evaluates the imaging plan 6 and executes various types of processing, similarly to the first embodiment.

On the contrary, if the value registered for the item, "Any Manual Adjustment", is "1", that is, if the imaging plan 6 has been adjusted manually, the evaluating function 15*a* does not evaluate the imaging plan 6. As described above, in this seventh modified example, if the imaging plan 6 has been adjusted manually, the evaluating function 15*a* does not evaluate the imaging plan 6 that has been adjusted.

In this case, the transmitting function 15*c* of the evaluation server 10 transmits a message, "Because the imaging plan has been adjusted manually, the imaging plan will not be evaluated." to the terminal device 4. The terminal device 4 then displays the message, "Because the imaging plan has been adjusted manually, the imaging plan will not be evaluated." on the display 44. A user is thereby able to know the reason why the imaging plan 6 is not to be evaluated.

However, even if the value registered for the item, "Any Manual Adjustment", is "1", the evaluating function 15*a* may evaluate the imaging plan 6 depending on conditions. For example, the evaluating function 15*a* determines whether or not at least one of an imaging condition, a reconstruction condition, and a postprocessing condition included in the imaging plan 6 has been updated after the date on which the imaging plan 6 transmitted from the terminal device 4 was adjusted.

If that at least one condition had been updated on or before the date on which the imaging plan 6 transmitted from the terminal device 4 was adjusted, the evaluating function 15*a* does not evaluate the imaging plan 6. In this case also, the transmitting function 15*c* transmits the message, "Because the imaging plan has been adjusted manually, the imaging plan will not be evaluated." to the terminal device 4.

On the contrary, if that at least one condition was updated after the imaging plan transmitted from the terminal device 4 had been adjusted, the evaluating function 15*a* evaluates the imaging plan 6 and executes various types of processing, similarly to the first embodiment. In this case, the transmitting function 15c of the evaluation server 10 transmits, together with the various types of information illustrated in FIG. 10, a message, "The imaging plan has been adjusted manually, but because a condition included in the imaging plan was updated after the imaging plan had been adjusted manually, the imaging plan was evaluated.", to the terminal device 4. The terminal device 4 then displays, together with the various types of information, the message, "The imaging plan has been adjusted manually, but because a condition included in the imaging plan was updated after the imaging plan had been adjusted manually, the imaging plan was evaluated.", on the display 44. A user is thereby able to know the reason why the imaging plan 6 was evaluated.

As described above, if an imaging plan 6 has been adjusted manually, the evaluating function 15a controls whether or not the imaging plan 6 that has been adjusted is to be evaluated, according to the time at which the imaging plan 6 was adjusted manually, and the time at which at least one of an imaging condition, a reconstruction condition, and a postprocessing condition included in the imaging plan 6 was updated.

Eighth Modified Example of First Embodiment

As described above, a specialist managing imaging plans may manually adjust imaging conditions, reconstruction conditions, postprocessing conditions, etc. that are included in the imaging plans.

There are plural types (machine models) of X-ray CT devices 5. A specialist tends to adjust an imaging plan corresponding to a specific type of X-ray CT devices 5 from the plural types of X-ray CT devices 5. That is, an imaging plan corresponding to a specific type of X-ray CT devices 5 is considered to be likely to have been adjusted by a specialist. Therefore, an imaging plan corresponding to a specific type of X-ray CT devices 5 is considered to be likely to be an imaging plan suitable for functions of the X-ray CT devices 5 and circumstances at a facility, such as a hospital 3. The evaluation server 10 may thus be configured to not evaluate an imaging plan corresponding to a specific type of X-ray CT devices 5. Such a modified example will thus be described below as an eighth modified example of the first embodiment. In describing the eighth modified example, components different from those of the first embodiment will be described mainly, and description of components that are the same as those of the first embodiment may be omitted.

Figures 18, 19:
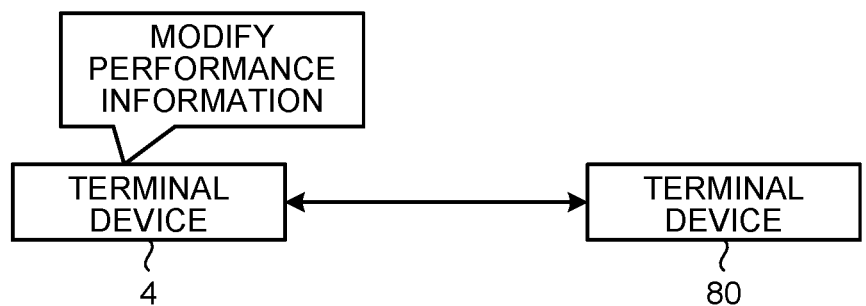
FIG. 18 is a diagram illustrating an example of a data structure of a performance information database according to an eighth modified example of the first embodiment.
FIG. 19 is a diagram illustrating an example of a configuration of a part of an evaluation system according to a ninth modified example of the first embodiment.

FIG. 18 is a diagram illustrating an example of a data structure of a performance information database 12b according to the eighth modified example of the first embodiment.

An evaluation server 10 according to the eighth modified example is different from the evaluation server 10 according to the first embodiment in that the evaluation server 10 according to the eighth modified example performs various types of processing using the performance information database 12b illustrated in FIG. 18 instead of the performance information database 12b illustrated in FIG. 7.

As illustrated in FIG. 18, in this eighth modified example, the performance information database 12b has, registered therein, plural records each having an item, "Machine Model ID", an item, "Performance Information", and an item, "Necessity of Execution of Evaluation". That is, each record registered in the performance information database 12b has an item, "Machine Model ID", an item, "Performance Information", and an item, "Necessity of Execution of Evaluation", in association with one another. The performance information database 12b has, registered therein, a plurality of these records.

Among these items, for the item, "Machine Model ID", and the item, "Performance Information", content similar to that in the first embodiment is registered.

For the item, "Necessity of Execution of Evaluation", a value indicating whether or not the evaluation server 10 is to evaluate the imaging plan 6 corresponding to the X-ray CT device 5 of the type registered for the item, "Machine Model ID", is registered. For example, if the X-ray CT device 5 of the type registered for the item, "Machine Model ID", is the specific CT device described above, "1", indicating that the evaluation server 10 is not to evaluate the imaging plan 6 is registered for the item, "Necessity of Execution of Evaluation". On the contrary, if the X-ray CT device 5 of the type registered for the item, "Machine Model ID", is not the specific CT device described above, "0", indicating that the evaluation server 10 is to evaluate the imaging plan 6 is registered for the item, "Necessity of Execution of Evaluation".

In this eight modified example, the evaluation requesting function 45c of the terminal device 4 transmits, in addition to the imaging plan 6 to be evaluated, the machine model ID 7, and the examination purpose 8 that are illustrated in FIG. 4, the value (0 or 1) registered for the item, "Necessity of Execution of Evaluation", to the evaluation server 10.

If the value registered for the item, "Necessity of Execution of Evaluation", is "0", the evaluating function 15a of the evaluation server 10 evaluates the imaging plan 6 and executes various types of processing, similarly to the first embodiment.

On the contrary, if the value registered for the item, "Necessity of Execution of Evaluation", is "1", the evaluating function 15a does not evaluate the imaging plan 6. As described above, in this eighth modified example, if the X-ray CT device 5 is the specific CT device, the evaluating function 15a does not evaluate the imaging plan 6.

In this case, the transmitting function 15c of the evaluation server 10 transmits a message, "Because the X-ray CT device is a specific CT device, the imaging plan is likely to have been adjusted manually and thus will not be evaluated." to the terminal device 4. The terminal device 4 then displays the message, "Because the X-ray CT device is a specific CT device, the imaging plan is likely to have been adjusted manually and thus will not be evaluated." on the display 44. A user is thereby able to know the reason why the imaging plan 6 is not evaluated.

Ninth Modified Example of First Embodiment

In the first embodiment, at Step S202 illustrated in FIG. 11, a user considers whether or not to modify the imaging plan 50 presented and further considers how to modify the imaging plan 50 if the imaging plan 50 is to be modified. The user then inputs a modification instruction via the input interface 43 to the processing circuitry 45 after considering how the imaging plan 50 is to be modified.

At Step S202, the user may receive advice from a specialist to modify the imaging plan 50. The evaluation system 1 that implements such modification will thus be described below as an evaluation system 1 according to the ninth modified example of the first embodiment.

FIG. 19 is a diagram illustrating an example of a configuration of a part of the evaluation system 1 according to the ninth modified example of the first embodiment. The devices and server illustrated in FIG. 1 other than a terminal device 4 and a terminal device 80 are not illustrated in FIG. 19.

As illustrated in FIG. 19, the evaluation system 1 according to the ninth modified example includes the terminal device 4, the terminal device 80, and the various devices and server (not illustrated in FIG. 19) already illustrated in FIG. 1.

The terminal device 4 is a terminal used by a user and the terminal device 80 is a terminal used by a specialist. The terminal device 4 and the terminal device 80 are connected to each other via a network. In this modified example, the terminal device 4 and the terminal device 80 each cause a chat screen to be displayed on a display and let the user and the specialist chat with each other online. Therefore, at Step S202 illustrated in FIG. 11, the user is able to consider how to modify the imaging plan 50 while receiving advice from the specialist. Therefore, the user is able to readily determine how the imaging plan 50 is to be modified.

Remote access to the terminal device 4 may be provided to the terminal device 80, and the terminal device 4 and the terminal device 80 may engage in video chat. In this case, just by operating the terminal device 80, the specialist is able to modify the imaging plan 50 displayed at the terminal device 4. That is, in this case, not only the user, but also the specialist who is at a location remote from the terminal device 4, is able to modify the imaging plan 50.

Furthermore, in a state where a phantom has been installed in the X-ray CT device 5, the terminal device 4 may receive operation by the user and remotely operate the X-ray CT device 5 to cause the X-ray CT device 5 to image the phantom and generate image data based on the imaging plan 50 and image data based on the imaging plan 6. In this case, a clinical radiologist is present at the X-ray CT device 5.

The terminal device 4 then may acquire the image data based on the imaging plan 50 and the image data based on the imaging plan 6, from the X-ray CT device 5 and display two images based on the two sets of image data acquired to be comparable to each other on the display 44.

Furthermore, the terminal device 4 may control the X-ray CT device 5 to retry reconstruction using the reconstruction conditions included in the imaging plans 50 and 6 by remotely operating the X-ray CT device 5. The terminal device 4 then may acquire results of the retry of reconstruction and display the results of the retry of reconstruction on the display 44.

Tenth Modified Example of First Embodiment

The case where at Step S138, the transmitting function 15c transmits the program of reconstruction processing and the program of postprocessing to the terminal device 4 has been described above with respect to the second modified example. The transmitting function 15c may transmit a program to the terminal device 4, the program being suitable for circumstances at a facility, such as a hospital 3, at which the terminal device 4 is provided. Such a modified example will thus be described below as a tenth modified example of the first embodiment. In describing the tenth modified example, components different from those of the second modified example will be described mainly, and description of components that are the same as those of the second modified example may be omitted.

FIG. 20A is a diagram illustrating an example of a data structure of a program database 81a according to the tenth modified example of the first embodiment. In this tenth modified example, the memory 12 stores the program database 81a illustrated in FIG. 20A.

As illustrated in FIG. 20A, the program database 81a has, registered therein, plural records each having an item, "Type of Hospital", an item, "Region", and an item, "Program". That is, each record registered in the program database 81a has an item, "Type of Hospital", an item, "Region", and an item, "Program", in association with one another. The program database 81a has, registered therein, a plurality of these records.

For the item, "Type of Hospital", the type of the hospital is registered. Types of hospitals include, for example, a type that specializes in specific diagnoses (examinations) and conduct specific examinations comparatively often, and a type that conducts diagnoses extensively.

For the item, "Region", a region to be diagnosed (to be examined) is registered.

For the item, "Program", the program of reconstruction processing and the program of postprocessing that match the type of hospital registered for the item, "Type of Hospital", and correspond to the region registered for the item, "Region", are registered.

In the tenth modified example, when causing the evaluation server 10 to evaluate the imaging plan 6, a user inputs the type of the hospital 3 and the region to be diagnosed, to the processing circuitry 45, via the input interface 43. In the tenth modified example, the evaluation requesting function 45c of the terminal device 4 then transmits, in addition to the imaging plan 6 to be evaluated, the machine model ID 7, and the examination purpose 8 that are illustrated in FIG. 4, the type of the hospital 3 and region to be diagnosed that have been input by the user, to the evaluation server 10.

At Step S138, the transmitting function 15c then acquires the program of reconstruction processing and the program of postprocessing that correspond to the type of the hospital 3 and the region to be diagnosed, from the program database 81a. The transmitting function 15c then transmits the program of reconstruction processing and program of postprocessing that have been acquired, to the terminal device 4. The X-ray CT device 5 is thereby able to execute the programs suitable for circumstances at the hospital 3 (the type).

Eleventh Modified Example of First Embodiment

The case where at Step S138, the transmitting function 15c transmits the program of reconstruction processing and the program of postprocessing that match the type of the hospital, to the terminal device 4, has been described above with respect to the tenth modified example. There are various types of X-ray CT devices 5. For example, at general hospitals each having many X-ray CT devices 5, the types of the X-ray CT devices 5 include a type for uses specialized in specific diagnoses (examinations) and a type used for various diagnoses and not specialized in specific diagnoses. Different types of X-ray CT devices 5 thus execute different programs.

The transmitting function 15c may thus transmit a program suitable for the type of the X-ray CT device 5, to the terminal device 4. Such a modified example will thus be described below as an eleventh modified example of the first embodiment. In describing the eleventh modified example, components different from those of the tenth modified example will be described mainly, and description of components that are the same as those of the tenth modified example may be omitted.

FIG. 20B is a diagram illustrating an example of a data structure of a program database 81b according to the eleventh modified example of the first embodiment. In this eleventh modified example, the memory 12 stores the program database 81b illustrated in FIG. 20B.

As illustrated in FIG. 20B, the program database 81b has, registered therein, plural records each having an item, "Type of Device", and an item, "Program". That is, each record registered in the program database 81b has an item, "Type of Device", and an item, "Program", in association with each other. The program database 81b has, registered therein, a plurality of these records.

For the item, "Type of Device", the type of the X-ray CT device 5 is registered. Types of X-ray CT devices 5 include, for example, as described above, a type for uses specialized in specific diagnoses and a type used for various diagnoses and not specialized in specific diagnoses.

For the item, "Program", a program of reconstruction processing and a program of postprocessing that match the type of the X-ray CT device 5 registered for the item, "Type of Device", are registered.

In the eleventh modified example, in causing the evaluation server 10 to evaluate the imaging plan 6, a user inputs the type of the X-ray CT device 5 to the processing circuitry 45 via the input interface 43. In the eleventh modified example, the evaluation requesting function 45c of the terminal device 4 then transmits, in addition to the imaging plan 6 to be evaluated, the machine model ID 7, and the examination purpose 8 that are illustrated in FIG. 4, the type of the X-ray CT device 5 input by the user, to the evaluation server 10.

At Step S138, the transmitting function 15c then acquires the program of reconstruction processing and the program of postprocessing that correspond to the type of the X-ray CT device 5, from the program database 81b. The transmitting function 15c then transmits the program of reconstruction processing and the program of postprocessing that have been acquired, to the terminal device 4. The X-ray CT device 5 is thereby able to execute the programs suitable for circumstances at the X-ray CT device 5 (the type).

Other Modified Examples

The following description relates to other modified examples. The case where the evaluation server 10 automatically evaluates the imaging plan 6 and automatically generates the imaging plan 50 that would make the radiation dose of X-rays received by a subject adequate has been described above with respect to the first embodiment and the modified examples. However, a specialist as described above may evaluate the imaging plan 6 received by the evaluation server 10 and generate an imaging plan that would make the radiation dose of X-rays received by a subject adequate, and the evaluation server 10 then may transmit the imaging plan generated by the specialist, to the terminal device 4.

Furthermore, the evaluation server 10 may implement generation of an imaging plan 50 by inputting the imaging plan 6 to a trained model that outputs, when an imaging plan is input to the trained model, an imaging plan by which a radiation dose received by a subject becomes adequate. The evaluation server 10 may then transmit the imaging plan 50 generated, to the terminal device 4.

Furthermore, a usage fee for the evaluation system 1 may be charged. For example, if presenting an imaging plan 50 in response to transmission of an imaging plan 6 is considered as a single process, a usage fee may be charged for each process. In addition, for a specified amount of money over a specified time period, presentation of an imaging plan 50 in response to transmission of an imaging plan 6 may be received any number of times.

The components of each device according to the embodiments described above have been functionally and conceptually illustrated in the drawings and are not necessarily configured physically as illustrated in the drawings. That is, specific forms of distribution and integration of the devices are not limited to those illustrated in the drawings, and all or a part of each device may be configured to be distributed or integrated functionally or physically in any units, according to various loads and/or use situations, for example. In addition, all or any part of the processing functions executed at the devices may be implemented by a central processing unit (CPU) and a program analyzed and executed by the CPU or implemented as hardware by wired logic.

Furthermore, any part of the processes described above with respect to the embodiments as being executed automatically may be executed manually instead, or all or a part of the processes described as being executed manually may be executed automatically by a known method instead. The processing procedures, control procedures, specific names, and information including various data and parameters, which have been described above and illustrated in the drawings, may be modified in any way except otherwise described specifically.

In addition, the term, "processor", used in the above description means for example: a CPU; a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). The processor implements its functions by reading and executing programs stored in a memory. Instead of being stored in the memory, the programs may be directly incorporated in a circuit of the processor. In that case, by reading and executing the programs incorporated in the circuit, the processor implements the functions. Each of the processors according to the embodiments is not necessarily configured as a single circuit, and plural independent circuits may be combined together to be configured as a single processor to implement their functions. Plural components in each drawing may also be integrated into a single processor to implement their functions.

Any of the methods described above with respect to the embodiments may be implemented by a computer executing a program (an evaluation program) that has been prepared in advance. The computer may be a personal computer or a work station. This program is provided by being incorporated into, for example, a read only memory (ROM) or a memory beforehand. The program may be provided by being stored in a computer-readable non-transitory storage medium, such as a compact disk (CD)-ROM, a flexible disk (FD), a CD-recordable (CD-R), or a digital versatile disk (DVD), as a file in a format installable or executable in the devices. The program may be provided or distributed by being stored on a computer connected to a network, such as the Internet, and being downloaded via the network. For example, the program is configured as modules including the above described functions. As to actual hardware, by a CPU reading and executing the program from a storage medium, such as a ROM, the modules are loaded and generated on a main storage.

At least one embodiment described above enables generation of the imaging plan 50 that is more appropriate.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirits of the inventions.

What is claimed is:

1. An evaluation apparatus, comprising:
processing circuitry configured to
based on performance information related to performance of a medical diagnostic imaging device and numerical information related to an evaluation item, make an evaluation of a first imaging plan used by the medical diagnostic imaging device, the numerical information conforming to a guideline related to imaging plans,
based on a result of the evaluation, generate, from the first imaging plan, a second imaging plan conforming to the guideline,
output the second imaging plan, which includes imaging conditions and reconstruction conditions, and
automatically control the medical diagnostic imaging device to perform an imaging scan of a subject using the imaging conditions included in the second imaging plan to generate imaging data of the subject, and reconstruct and display an image of the subject using the imaging data and the reconstruction conditions included in the second imaging plan.

2. The evaluation apparatus according to claim 1, wherein the numerical information is a range of numerical values related to the evaluation item, and
the processing circuitry is further configured to generate the second imaging plan such that:
a numerical value related to the evaluation item falls within the range of numerical values related to the evaluation item; and
a difference between an image quality of first image data and an image quality of second image data becomes equal to or less than a threshold, the first image data being acquired in a case where the medical diagnostic imaging device performs imaging using the first imaging plan, the second image data being acquired in a case where the medical diagnostic imaging device performs imaging using the second imaging plan.

3. The evaluation apparatus according to claim 1, wherein the numerical information is a range of numerical values related to the evaluation item, and
the processing circuitry is further configured to generate the second imaging plan such that:
a numerical value related to the evaluation item falls within the range of numerical values related to the evaluation item; and
an image quality of second image data becomes higher than an image quality of first image data acquired in a case where the medical diagnostic imaging device performs imaging using the first imaging plan, the second image data being acquired in a case where the medical diagnostic imaging device performs imaging using the second imaging plan.

4. The evaluation apparatus according to claim 2, wherein the processing circuitry is further configured to generate the second imaging plan such that a difference between the numerical value related to the evaluation item and a specific value in the range of numerical values related to the evaluation item becomes equal to or less than a threshold.

5. The evaluation apparatus according to claim 1, wherein the processing circuitry is further configured to:
predict
first image data acquired in a case where the medical diagnostic imaging device performs imaging using the first imaging plan; and
second image data acquired in a case where the medical diagnostic imaging device performs the imaging using the second imaging plan, and
output the result of the evaluation, the first image data, and the second image data.

6. The evaluation apparatus according to claim 1, wherein the processing circuitry is further configured to output the first imaging plan.

7. The evaluation apparatus according to claim 1, wherein the processing circuitry is configured to acquire the evaluation item, which is a radiation dose of X-rays received by a subject, and
the numerical information is a range of radiation doses of X-rays.

8. The evaluation apparatus according to claim 7, wherein the first imaging plan includes a first imaging condition used by the medical diagnostic imaging device,
the performance information includes second imaging conditions used by the medical diagnostic imaging device, and
in a case where any second imaging condition that is not used by the medical diagnostic imaging device even though using that second imaging condition enables reduction of the radiation dose is present in the second imaging conditions, the processing circuitry is further configured to generate the second imaging plan by changing the first imaging condition included in the first imaging plan to that second imaging condition not used by the medical diagnostic imaging device.

9. The evaluation apparatus according to claim 7, wherein the first imaging plan includes a first reconstruction condition used by the medical diagnostic imaging device,
the performance information includes second reconstruction conditions used by the medical diagnostic imaging device, and
in a case where any second reconstruction condition that is not used by the medical diagnostic imaging device even though using that second reconstruction condition enables reduction of the radiation dose is present in the second reconstruction conditions, the processing circuitry is further configured to generate the second imaging plan by changing the first reconstruction condition included in the first imaging plan to that second reconstruction condition not used by the medical diagnostic imaging device.

10. The evaluation apparatus according to claim 7, wherein
the first imaging plan includes a first postprocessing condition used by the medical diagnostic imaging device,
the performance information includes second postprocessing conditions used by the medical diagnostic imaging device, and
in a case where any second postprocessing condition that is not used by the medical diagnostic imaging device even though using that second postprocessing condition enables reduction of the radiation dose is present in the second postprocessing conditions, the processing circuitry is further configured to generate the second imaging plan by changing the first postprocessing condition included in the first imaging plan to that second postprocessing condition not used by the medical diagnostic imaging device.

11. The evaluation apparatus according to claim 9, wherein the processing circuitry is further configured to:
estimate an image quality of image data acquired by the medical diagnostic imaging device performing imaging using the second imaging plan in the case where the second reconstruction condition that is not used by the medical diagnostic imaging device even though using that second reconstruction condition enables reduction of the radiation dose is present; and
determine that the radiation dose of X-rays received by the subject is higher than the range of radiation doses in a case where the image quality estimated is equal to or higher than a threshold.

12. The evaluation apparatus according to claim 10, wherein the processing circuitry is further configured to:
estimate an image quality of image data acquired by the medical diagnostic imaging device performing the imaging using the second imaging plan in the case where the second postprocessing condition that is not used by the medical diagnostic imaging device even though using the second postprocessing condition enables reduction of the radiation dose is present; and
determine that the radiation dose of X-rays received by the subject is higher than the range of radiation doses in a case where the image quality estimated is equal to or greater than a threshold.

13. The evaluation apparatus according to claim 12, wherein the processing circuitry is further configured to determine that the radiation dose of X-rays received by the subject is lower than the range of radiation doses in a case where the image quality estimated is less than the threshold.

14. The evaluation apparatus according to claim 7, wherein the processing circuitry is further configured to:
estimate a radiation dose in a case where the medical diagnostic imaging device performs the imaging using the first imaging plan; and
determine that the radiation dose of X-rays received by the subject is in the range of radiation doses in a case where the radiation dose estimated is in the range of radiation doses.

15. The evaluation apparatus according to claim 14, wherein the processing circuitry is further configured to determine that the radiation dose of X-rays received by the subject is outside the range of radiation doses in a case where the radiation dose estimated is outside the range of radiation doses.

16. The evaluation apparatus according to claim 1, wherein the processing circuitry is further configured to output information in a case where an update of at least one of the performance information and the numerical information has been made, the information indicating that the at least one of the performance information and the numerical information has been updated.

17. The evaluation apparatus according to claim 1, wherein in a case where an update of at least one of the performance information and the numerical information has been made, the processing circuitry is further configured to output: a second imaging plan based on the performance information and the numerical information of a time before the update of the at least one of the performance information and the numerical information; and a second imaging plan based on the performance information and the numerical information of a time after the update of the at least one of the performance information and the numerical information.

18. The evaluation apparatus according to claim 1, wherein in a case where an update of at least one of the performance information and the numerical information has been made, the processing circuitry is further configured to output, for a predetermined time period from the update of the at least one of the performance information and the numerical information: a second imaging plan based on the performance information and the numerical information of a time before the update of the at least one of the performance information and the numerical information; and a second imaging plan based on the performance information and the numerical information of a time after the update of the at least one of the performance information and the numerical information.

19. The evaluation apparatus according to claim 1, wherein in a case where an update of at least one of the performance information and the numerical information has been made, the processing circuitry is further configured to output information that enables comparison between: the at least one of the performance information and the numerical information of a time before the update; and the at least one of the performance information and the numerical information of a time after the update.

20. The evaluation apparatus according to claim 1, wherein in a case where the performance information has been updated and an updated condition included in the performance information and a specified condition match each other, the processing circuitry is further configured to output the updated condition.

21. The evaluation apparatus according to claim 1, wherein in a case where the first imaging plan has been adjusted manually, the processing circuitry is further configured to not evaluate the first imaging plan that has been adjusted.

22. The evaluation apparatus according to claim 1, wherein in a case where the first imaging plan has been adjusted manually, the processing circuitry is further configured to control whether or not to evaluate the first imaging plan that has been adjusted, according to: the time at which the first imaging plan was adjusted manually; and the time at which the performance information was updated.

23. The evaluation apparatus according to claim 1, wherein the processing circuitry is further configured to not evaluate the first imaging plan in a case where the medical diagnostic imaging device is a specific medical diagnostic imaging device.

24. The evaluation apparatus according to claim 1, wherein the processing circuitry is further configured to output a program that is included in the second imaging plan, that is not included in the first imaging plan, and that matches a type of a facility in which the medical diagnostic imaging device has been installed.

25. The evaluation apparatus according to claim 1, wherein the processing circuitry is further configured to output a program that is included in the second imaging plan, that is not included in the first imaging plan, and that matches a type of the medical diagnostic imaging device.

26. An evaluation method, including:
based on performance information related to performance of a medical diagnostic imaging device and numerical information related to at least one evaluation item, making an evaluation of a first imaging plan used by the medical diagnostic imaging device, the numerical information conforming to a guideline related to imaging plans;

based on a result of the evaluation, generating, from the first imaging plan, a second imaging plan conforming to the guideline;

controlling to output the second imaging plan, which includes imaging conditions and reconstruction conditions, and automatically controlling the medical diagnostic imaging device to perform an imaging scan of a subject using the imaging conditions included in the second imaging plan to generate imaging data of the subject, and reconstructing and displaying an image of the subject using the imaging data and the reconstruction conditions included in the second imaging plan.

27. An evaluation system, comprising:

an evaluation apparatus; and a terminal device, wherein the evaluation apparatus comprises first processing circuitry configured to based on performance information related to performance of a medical diagnostic imaging device and numerical information related to at least one evaluation item, make an evaluation of a first imaging plan used by the medical diagnostic imaging device, the numerical information conforming to a guideline related to imaging plans, based on a result of the evaluation, generate, from the first imaging plan, a second imaging plan conforming to the guideline, and output the second imaging plan, which includes imaging conditions and reconstruction conditions, and the terminal device comprises second processing circuitry configured to cause the second imaging plan to be displayed by a display device, and automatically control the medical diagnostic imaging device to perform an imaging scan of a subject using the imaging conditions included in the second imaging plan to generate imaging data of the subject, and reconstruct and display an image of the subject using the imaging data and the reconstruction conditions included in the second imaging plan.

* * * * *